United States Patent
Wall et al.

(10) Patent No.: US 12,398,152 B2
(45) Date of Patent: Aug. 26, 2025

(54) THIOXANTHONE DERIVATIVES, COMPOSITION COMPRISING THE SAME AND PATTERN FORMING METHOD COMPRISING SAID COMPOSITION

(71) Applicants: LINTFIELD LIMITED, Tonbridge (GB); TOKYO ELECTRON LIMITED, Tokyo (JP)

(72) Inventors: Christopher Wall, Tonbridge (GB); Seiji Nagahara, Tokyo (JP)

(73) Assignees: LINTFIELD LIMITED, Tonbridge (GB); TOKYO ELECTRON LIMITED, Tokyo (JP)

( * ) Notice: Subject to any disclaimer, the term of this patent is extended or adjusted under 35 U.S.C. 154(b) by 1207 days.

(21) Appl. No.: 17/261,267

(22) PCT Filed: Jul. 18, 2019

(86) PCT No.: PCT/EP2019/069451
§ 371 (c)(1),
(2) Date: Jan. 19, 2021

(87) PCT Pub. No.: WO2020/016389
PCT Pub. Date: Jan. 23, 2020

(65) Prior Publication Data
US 2021/0277017 A1    Sep. 9, 2021

(30) Foreign Application Priority Data

Jul. 19, 2018 (GB) .................................... 1811800
Nov. 30, 2018 (GB) .................................... 1819586

(51) Int. Cl.
*C07D 495/10* (2006.01)
*C07D 335/16* (2006.01)
(Continued)

(52) U.S. Cl.
CPC ......... *C07D 495/10* (2013.01); *C07D 335/16* (2013.01); *C07D 495/04* (2013.01);
(Continued)

(58) Field of Classification Search
CPC .. C07D 495/10; C07D 335/16; C07D 495/04; C07D 495/20; G03F 7/0045; G03F 7/031
See application file for complete search history.

(56) References Cited

U.S. PATENT DOCUMENTS 4,491,628 A    1/1985   Ito et al.
4,661,595 A    4/1987   Avar
(Continued)

FOREIGN PATENT DOCUMENTS

EP    2792694 A1    10/2014
EP    3109703 A1    12/2016
(Continued)

OTHER PUBLICATIONS

Karasu, F.; Arsu, N.; Jockusch, S.; Turro, N.J. "Thioxanthone Hydroquinone-O,O'-diacetic Acid: Photoinitiator or Photostabilizer?" J. Org. Chem. 2013, 78, 9161-9165. (Year: 2013).*

(Continued)

*Primary Examiner* — Andrew D Kosar
*Assistant Examiner* — John D McAnany
(74) *Attorney, Agent, or Firm* — MERCHANT & GOULD P.C.

(57) ABSTRACT

Latent photoinitiator compounds are described, as well as compositions containing such compounds and their uses in photoinitiated methods for producing photoresist structures.

16 Claims, 15 Drawing Sheets

(51) Int. Cl.

| | |
|---|---|
| C07D 495/04 | (2006.01) |
| C07D 495/20 | (2006.01) |
| G03F 7/004 | (2006.01) |
| G03F 7/031 | (2006.01) |
| G03F 7/039 | (2006.01) |

(52) U.S. Cl.
CPC ......... *C07D 495/20* (2013.01); *G03F 7/0045* (2013.01); *G03F 7/031* (2013.01); *G03F 7/0392* (2013.01)

(56) References Cited

U.S. PATENT DOCUMENTS

| | | | |
|---|---|---|---|
| 5,414,092 | A | 5/1995 | Green |
| 6,136,499 | A | 10/2000 | Goodall et al. |
| 7,126,011 | B2 | 10/2006 | Berg |
| 7,425,585 | B2 | 9/2008 | Kura et al. |
| 7,585,611 | B2 | 9/2009 | Kato et al. |
| 7,858,287 | B2 | 12/2010 | Watanabe et al. |
| 8,614,047 | B2 | 12/2013 | Ayothi et al. |
| 9,529,259 | B2 | 12/2016 | Namai |
| 2004/0014833 | A1 | 1/2004 | Bradley |
| 2011/0086389 | A1 | 4/2011 | Dolly et al. |
| 2013/0105297 | A1* | 5/2013 | Johnstone ............... B01J 19/123 252/183.11 |
| 2014/0014833 | A1 | 1/2014 | Sekiya |
| 2014/0120469 | A1 | 5/2014 | Prokopowicz et al. |
| 2015/0060728 | A1 | 3/2015 | Enomoto et al. |
| 2015/0241783 | A1 | 8/2015 | Carcasi et al. |
| 2016/0327869 | A1 | 11/2016 | Nagahara et al. |
| 2016/0357103 | A1 | 12/2016 | Nagahara et al. |
| 2017/0052449 | A1* | 2/2017 | Nakagawa ................ G03F 7/38 |

FOREIGN PATENT DOCUMENTS

| | | | | |
|---|---|---|---|---|
| EP | 3133444 | A1 * | 2/2017 | ........... C07C 303/32 |
| GB | 2476976 | A | 7/2011 | |
| JP | 2009-015115 | A | 1/2009 | |
| JP | 5964242 | | 8/2016 | |
| WO | 2002012350 | A2 | 2/2002 | |
| WO | 2002040464 | A1 | 5/2002 | |
| WO | 2002048113 | A1 | 6/2002 | |
| WO | 2007030089 | A1 | 3/2007 | |
| WO | 2016100864 | A1 | 6/2016 | |

OTHER PUBLICATIONS

S. Tagawa, S. Enomoto, A. Oshima; Super High Sensitivity Enhancement by Photo-Sensitized Chemically Amplified Resist (PS-CAR) Process; Journal of Photopolymer Science and Technology; vol. 26, No. 6 (2013) 835-830.
Nagahara et al., "Photosensitized Chemically Amplified ResistTM (PSCARTM) 2.0 for high throughput and high resolution EUV lithography: Dual photosensitization of acid generation and quencher decomposition by flood exposure", Proc. SPIE10146, Advances in Patterning Materials and Processes XXXIV (2017) 10146-59.
Chapter 3.7 "Substituted thioxanthones", Industrial photoinitiators: A technical guide (Taylor & Francis Group, 2010) 60-64.
Catsoulacos, P., "The conversion of thioxanth-10-one 5,5-dioxide oxime acetates to amines by means of diborane reduction", Journal of Heterocyclic Chemistry, vol. 4, No. 4 (1967) 645-646.
Tagawa, S., et al., "High-resist sensitization by pattern and flood combination lithography", Proc. SPIE (2014) 9048, 90481S-1; https://www.spiedigitallibray.org/conference-proceedings of-spie.
Schmidt, M., et al., "New 1,3-dioxolane and 1,3-dioxane derivatives as effective modulators to overcome multidrug resistance", Bioorganic & Medicinal Chemistry, (2007)15(6), 2283-2297.
Roberts, K.C. and Samuel Smiles, "CXIII.—Methoxy-derivatives of thioxanthone", Journal of the Chemical Society (1929) 863-872.
McOmie, J.F.W., et al., "Demethylation of aryl methyl ethers by boron tribromide", Tetrahedron, 24:5 (1968), 2289-2292.
Le Grand, B., et al., "Na+ Currents in Cardioprotection: Better to Be Late", Journal of Medicinal Chemistry, 52(14) (2009) 4149-4160.
"Organic Resist Materials", Introduction to Microlithography, second edition, L. F. Thompson, C. Grant Willson, M. J. Bowden (eds), American Chemical Society (1994) 216-227.
Tartaglia Sabina, et al., "A Chemical/Computational Approach to the Determination of Absolute Configuration of Flexible and Transparent Molecules: Aliphatic Diols As a CaseStudy", J.Org.Chem., 73 (2008) 4865-4873.
Sharghi, H., et al., "Synthesis of some novel thioxanthenone-fused azacrown esther, and their use as new catalysts in the efficient, mind and regioselective conversion of epoxides to [bets]-hydroxy thiocyanates with ammonium hiocyanate", Helvetica Chimica Acta, vol. 90, No. 7 (2007) 1373-1385.
GB search report dated Jun. 3, 2019 in GB 1819586.7.
International Search Report mailed Nov. 13, 2019 in PCT/EP2019/069451.
Office Action dated Dec. 28, 2022 issued in equivalent Taiwanese Application No. 11121274490 and English Translation.
Office Action dated Jun. 27, 2023 issued in equivalent Japanese Application No. 2021-525374 and English Translation.
Office Action issued in corresponding Korean Patent Application No. 10-2021-7004816, Apr. 25, 2024.
STN Registry No. 858840-73-0(Entered STN: Aug. 8, 2005).
STN Registry No. 876494-01-8 (Entered STN:Mar. 12, 2006).
STN Registry No. 000813-64-8 (Entered STN: Jan. 25, 2008).

* cited by examiner

THIOXANTHONE DERIVATIVES, COMPOSITION COMPRISING THE SAME AND PATTERN FORMING METHOD COMPRISING SAID COMPOSITION

RELATED APPLICATIONS

The present application is a U.S. National Stage filing under 35 U.S.C. § 371 of International Application No. PCT/EP2019/069451 filed 18 Jul. 2019, which claims priority to GB Application No. 1811800.0 filed 19 Jul. 2018 and GB Application No. 1819586.7 filed 30 Nov. 2018.

FIELD OF THE INVENTION

The present invention relates to substituted thioxanthone derivatives in which the carbonyl group is blocked by an acyclic ketal or a substituted or an unsubstituted 1,3 dioxolane group or a substituted or an unsubstituted 1,3-dioxane group or a substituted or unsubstituted 1,3-dioxepane group or a substituted or an unsubstituted 1,3-dioxocane group or a substituted or an unsubstituted 1,3-dioxonane group, and to the use of such derivatives in photoinitiated reactions. The invention also relates to synthetic methods of making these and other substituted thioxanthone derivatives.

BACKGROUND OF THE INVENTION

Light absorbing ketone compounds are well known for use in photoinduced reactions. These species are commonly referred to as photoinitiators or photosensitisers and create reactive species when exposed to radiation. Examples of such photoinitiators or photosensitisers can be found in U.S. Pat. No. 7,585,611 B, EP 2,792,694 A1 and U.S. Pat. No. 7,425,585 B. When incorporated in a suitable transformable substrate, the reactive species generated by exposure to radiation, optionally in combination with other species, is capable of directly or indirectly, via a sensitisation and energy or electron transfer process, causing a chemical reaction in the transformable substrate. Typically, transformable substrates contain an organic material, which may be a monomer, oligomer, polymer, or mixture thereof, which is transformed to a new polymeric material.

In some applications, it is desirable to block the ketone moiety or moieties of ketone photoinitiators so that the photoinitiator is latent, and can be activated by deblocking. US 2004/0014833 and WO 2011/086389 relate to such protected ketone photoinitiators, and methods of using them.

The present invention is concerned with blocked or latent ketone photoinitiators which are improved over those known in the art. In particular, the blocked or latent ketone photoinitiators of the present invention having particular substituents and/or protecting groups on the carbon skeleton of the thioxanthone have been found to have properties which make them desirable in a variety of applications. These properties include an increased solubility difference of at least the deprotected species in an aqueous or organic developing media, compared to the unsubstituted photoinitiators.

Unless otherwise stated, references herein to a "blocked" ketone photoinitiator are to a latent ketone photoinitiator in which the ketone group has been blocked through reaction of the ketone with a diol to form a 1,3-dioxolane group, a 1,3-dioxane group, a 1,3-dioxepane group, a 1,3-dioxocane group or a 1,3-dioxonane group. Consequentially, references herein to a "unblocked" or "deblocked" ketone photoinitiator are to the active ketone photoinitiator with the carbonyl present in place of the 1,3-dioxolane group or 1,3-dioxane group or 1,3-dioxepane group or 1,3-dioxocane group or 1,3-dioxonane group. Unless otherwise stated, references herein to a "protected" ketone photoinitiator are to a compound having functional groups present on the aromatic ring of the photoinitiator, which functional groups have been modified by inclusion of a protecting group. For example, acetal, alkylcarbonate and ester substituents are protecting groups for an underlying hydroxy group and so a compound having one of these protecting groups as a substituent may be referred to as a protected ketone photoinitiator.

One particular application of blocked ketone photoinitiators to which the compounds of the present invention are suited is use as components of photoresist compositions. Photoresists are light-sensitive compositions used in many industrial processes and have particularly important applications in the electronics industry. Typically, photoresist compositions are coated on a substrate to form a photoresist layer. Selected regions of the layer are then exposed to electromagnetic energy, usually light energy, such as UV, deep UV, KrF or ArF excimer laser light, EUV light, or electron beam (EB) in order to initiate chemical reactions in the exposed regions of the photoresist. A photoresist developer is then used to remove material which is soluble in the developer. Photoresists can be in the form of negative photoresists or positive photoresists. A positive photoresist is a photoresist in which the exposed portion of the photoresist becomes soluble to the photoresist developer and can thus be removed by the developer, while the unexposed portion of the photoresist remains insoluble to the photoresist developer. A negative photoresist is one in which the exposed portion of the photoresist becomes insoluble to the photoresist developer while the unexposed portion of the photoresist is dissolved and can be removed by the photoresist developer. After the step using the developer, a patterned coating which is insoluble in the developer remains on the surface. Further steps may be carried out to harden the coating, such as a curing step which may be performed by the application of heat or further exposure to light.

Where features in the soluble parts of the photoresist which are to be removed by the developer are very fine, which is commonly the case for positive photoresists, it is important that the species present in the regions to be removed are soluble in the developer medium, which is typically an aqueous medium. Otherwise, so-called "scumming" can result. The latent, or blocked, photoinitiators described herein, may advantageously be used in such photoinitiated methods.

SUMMARY OF THE INVENTION

According to the present invention there is provided a compound of the formula I:

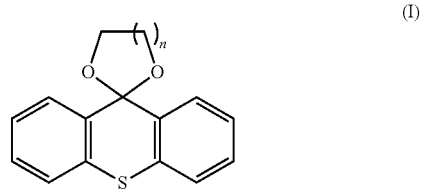

wherein n=1, 2, 3, 4 or 5 and wherein one or both of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio.

In an embodiment, one of the aromatic rings is substituted with at least one (e.g. one, two, three or four) substituents independently selected from hydroxy, alkoxy, benzyloxy, alkylcarbonate, hydroxyalkyl, acetal, ester, oxyacetic acid and esters thereof, aryloxy and arylthio and the other aromatic ring is unsubstituted. In another embodiment, each of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio. In this embodiment, each of the rings is substituted with a single substituent independently selected from hydroxy, alkoxy, benzyloxy, alkylcarbonate, hydroxyalkyl, acetal, ester, oxyacetic acid and esters thereof, aryloxy and arylthio, or one of the rings is substituted with two substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio or one of the rings is substituted with three substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio or one of the rings is substituted with four substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio.

In other embodiments, each of the aromatic rings is substituted with at least two substituents, for example at least three substituents, for example four substituents, each independently selected from hydroxy, alkoxy, benzyloxy, alkylcarbonate, hydroxyalkyl, acetal, ester, oxyacetic acid and esters thereof, aryloxy and arylthio.

In some embodiments, the 1,3-dioxolane ring, the 1,3-dioxane ring, the 1,3-dioxepane ring, the 1,3-dioxocane ring or the 1,3-dioxonane ring may be unsubstituted. In some embodiments, the 1,3-dioxolane ring, the 1,3-dioxane ring, the 1,3-dioxepane ring, the 1,3-dioxocane ring or the 1,3-dioxonane ring may be substituted with one or more substituent selected from alkyl, cycloalkyl, chloroalkyl, aryl or vinyl in any substitution pattern, for example geminal, vicinal or other. In some examples, (chloro)alkyl comprises C1-6 (chloro)alkyl, for example (chloro)methyl, (chloro) ethyl, (chloro)propyl, and also comprises (chloro)cycloalkyl in which two substituents on the for example 1,3-dioxane ring may be joined to form a cyclic group, for example a 5- or 6-membered carbocycle fused to the 1,3-dioxane ring. In some examples, the 1,3-dioxolane ring, the 1,3-dioxane ring, the 1,3-dioxepane ring, the 1,3-dioxocane ring or the 1,3-dioxonane ring may be substituted with one or more C1-6 alkyl groups, for example two or more C1-6 alkyl groups in any substitution pattern. For example, the 1,3-dioxolane ring, the 1,3-dioxane ring, the 1,3-dioxepane ring, the 1,3-dioxocane ring or the 1,3-dioxonane ring may be substituted with geminal or vicinal C1-6 alkyl groups, for example geminal or vicinal methyl groups. In some examples, the 1,3-dioxolane ring, the 1,3-dioxane ring, the 1,3-dioxepane ring, the 1,3-dioxocane ring or the 1,3-dioxonane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

In some examples, the compounds of the present invention are other than those of formula I, and can be based on the same thioxanthone ketone photoinitiator with the ketone blocked by an acyclic ketal, for example compounds in which the ketone is "blocked" by two alkoxy groups, for example two ethoxy groups. Such compound may be described as being compounds of formula Ia:

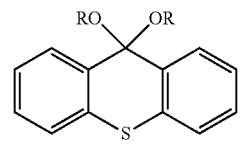

in which R=methyl, ethyl or propyl and wherein one or both of the aromatic rings is substituted with at least one substituent independently selected from hydroxy, alkoxy, benzyloxy, alkylcarbonate, hydroxyalkyl, acetal, ester, oxyacetic acid and esters thereof, 5 aryloxy and arylthio. Particularly preferred compounds of this type include: 9,9-diethoxy-3,4-dimethoxy-thioxanthene, 2-methoxy-6,6-dipropoxy-thiochromeno[3,2-g][1,3]benzodioxole, and 6,6-diethoxy-2-methoxy-thiochromeno[2,3-e][1,3]benzodioxole.

The invention also provides a composition comprising:
(a) a compound of formula I or Ia as defined above; and
(b) a chemically transformable substrate;
wherein the compound of formula I or Ia is a precursor of a reactive derivative of formula II:

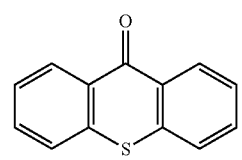 [SMILES: O=c1c2ccccc2sc2ccccc12]

(II)

the compound of formula II having the same substitution pattern as the compound of formula I or Ia and being obtainable by reacting the compound of formula I or Ia in the presence of an acid;
and further wherein the transformable substrate is capable of being transformed in the presence of the compound of formula II by a direct photoinitiated reaction or an indirect photoinitiated reaction.

In some examples, the compound of formula II having the same substitution pattern as the compound of formula I or Ia is obtainable by reacting the compound of formula I in the presence of an acid with heat treatment.

By "reactive derivative", it is meant that the acid treatment, with or without heat, cleaves the ketal, e.g. an acyclic ketal such as a diethyl ketal, or a cyclic ketal such as the 1,3-dioxane or 1.3-dioxolane or 1,3-dioxepane or the 1,3-dioxocane or the 1,3-dioxonane moiety to make available the carbonyl group which provides the reactive functionality in a photoinitiated method as described below.

The composition of the invention may be used in a photoinitiated method which comprises:
  (a) forming a layer of the composition on a support;
  (b) applying an acid, or generating an acid in situ, in selected regions of the layer and permitting the acid to react with the compound of formula I or Ia and form the reactive derivative of formula II in said selected regions of the layer;
  (c) exposing the layer with the reactive derivative present in said selected regions to electromagnetic radiation of a wavelength or energy suitable to generate a reactive species from the compound of formula II; and
  (d) permitting the reactive species directly or indirectly to cause transformation of the transformable substrate.

In some embodiments, permitting the acid to react with the compound of formula I or Ia and form the reactive derivative of formula II may comprise application of heat. The application of heat may be simultaneous with the applying of an acid or generating an acid in situ, or it may be subsequent to this step.

In some embodiments, the method may further comprise performing a post-transformation heat treatment.

The temperature of either one or both of these heat treatments may be in the range of from 70° C. to 170° C. The duration of either one or both of these heat treatment may be in the range of from 2 min to 120 min. It will be understood that the temperatures and times are provided merely by way of example and should not be considered in any way limiting.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, acetal, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, acetal, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, acetal, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, acetal, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, acetal, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, acetal, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, acetal, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, acetal, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, acetal, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, alkylcarbonate, hydroxyalkyl, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, acetal, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, acetal, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, acetal, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, acetal, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, benzyloxy, hydroxyalkyl, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, acetal, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, ester, oxyacetic acid, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, alkylcarbonate, hydroxyalkyl, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, acetal, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, ester, oxyacetic acid and esters thereof, aryloxy and arylthio.

In some embodiments, the reactive derivative of formula II comprises a compound of formula II in which one or both of the aromatic rings is substituted with at least one substituent independently selected from hydroxy, alkoxy, hydroxyalkyl, oxyacetic acid, aryloxy and arylthio.

For the avoidance of doubt, references in the preceding paragraphs to "one or both of the aromatic rings substituted with at least one substituent independently selected from . . . " are to situations in which each of the aromatic rings is singly substituted, or doubly substituted, or triply substituted, or quadruply substituted with each substituent being independently selected from any list provided herein. It will be understood that the same reference applies equally to situations in which one ring has a single substituent and the other has two, three or four substituents, or situations in which one ring has two substituents and the other has three or four substituents, or situations in which one ring has three substituents and the other has four substituents, with the substituents in all cases being independently selected from any list provided herein.

In some embodiments of the invention, compounds of the invention, have good solubility in an aqueous medium which makes them suitable for use in photoinitiated methods in which the compounds will remain after transformation of the chemically transformable substrate, and have to be removed by means of an aqueous developer solution.

In another embodiment, the compounds of the invention have much better solubility in aqueous media, after deprotection, which makes them suitable for use in photoinitiated methods in which the compounds themselves, and in particular the deprotected forms thereof, will remain after transformation of the chemically transformable substrate, and have to be removed by means of an aqueous developer solution resulting in an improved contrast and better image quality after development.

DESCRIPTION OF THE FIGURES

FIG. 1 shows the UV spectrum of 2,3-dimethoxy-9H-thioxanthen-9-one;

FIG. 2 shows the UV spectrum of 2,3-dihydroxy-9H-thioxanthen-9-one;

FIG. 3 shows the UV spectrum of 2,3,5-trimethoxy-9H-thioxanthen-9-one;

FIG. 4 shows the UV spectrum of 2,3,7-trimethoxy-9H-thioxanthen-9-one;

FIG. 5 shows the UV spectrum of 1,5,6-trihydroxy-9H-thioxanthen-9-one;

FIG. 6 shows the UV spectrum of 1,5,6-trimethoxy-9H-thioxanthen-9-one;

FIG. 7 shows the UV spectrum of 3,4-dihydroxy-9H-thioxanthen-9-one;

FIG. 8 shows the UV spectrum of 3,4-dimethoxy-9H-thioxanthen-9-one;

FIG. 9 shows the UV spectrum of 3',4'-dimethoxyspiro[1,3-dioxane-2,9'-thioxanthene];

FIG. 10 shows the UV spectrum of 2',3'-dimethoxyspiro[(1.3)-dioxolane-2,9'-thioxanthene];

FIG. 11 shows the UV spectrum of 3',4'-dimethoxy-4,6-dimethyl-spiro[1,3-dioxane-2,9'-thioxanthene];

FIG. 12 shows the UV spectrum of 2'-methoxyspiro[1,3-dioxepane-2,6'-thiochromeno[2,3-e][1,3]benzodioxole];

FIG. 13 shows the UV spectrum of 2'-methoxy-5,5-dimethyl-spiro[1,3-dioxane-2,6'-thiochromeno[2,3-e][1,3]benzodioxole];

DETAILED DESCRIPTION OF THE INVENTION

Compounds of the Invention

Figure 1:
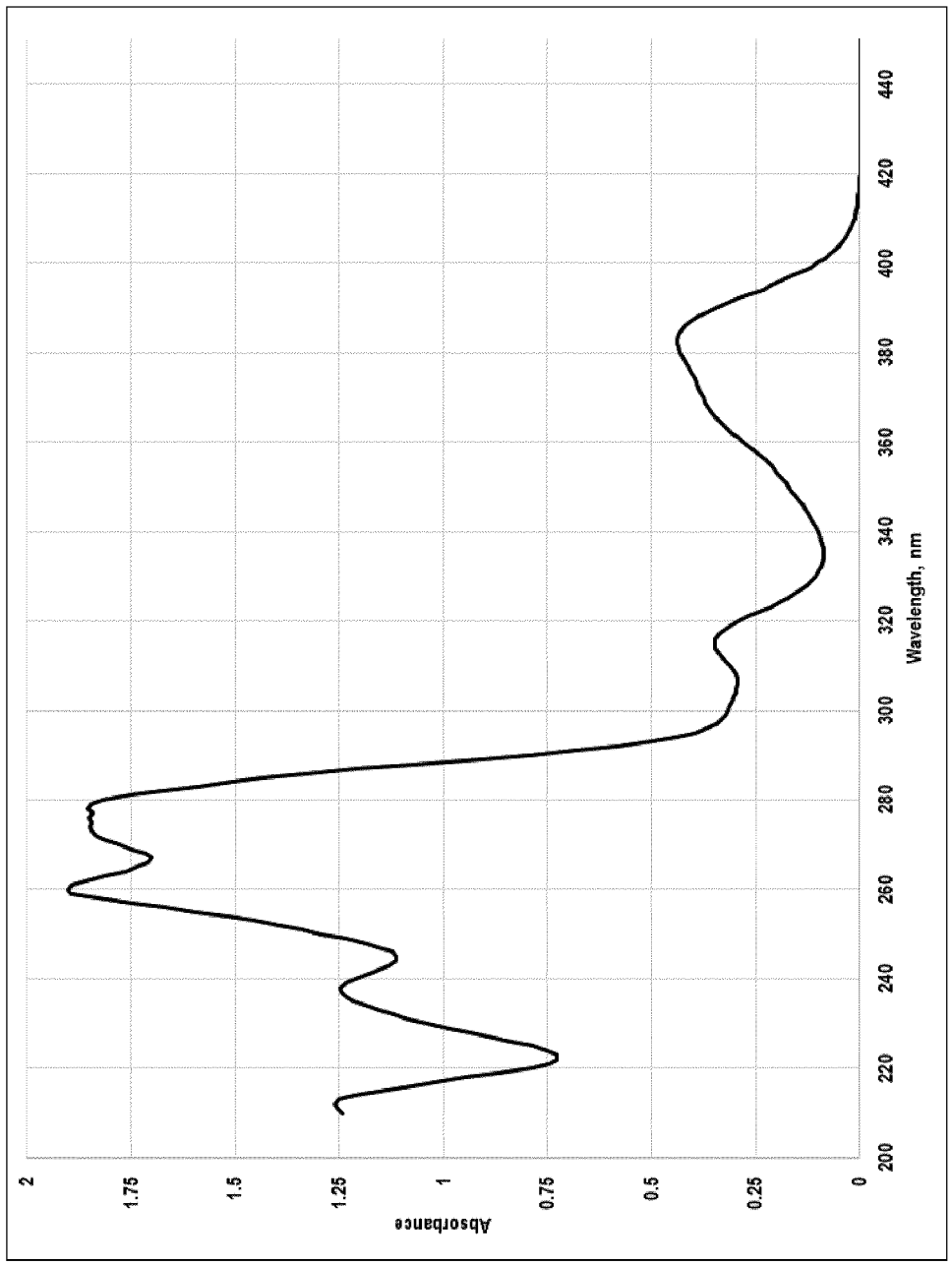
FIGS. 1 to 13 show the UV spectra of various compounds of the present invention, at 0.0008% in Acetonitrile, as follows.

In a first aspect, the present invention provides compounds of the formula I:

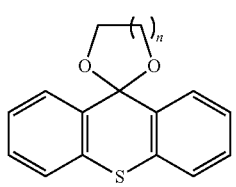

(I)

wherein n=1, 2, 3, 4 or 5 and wherein one or both of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio.

The present invention also provides compounds of formula Ia:

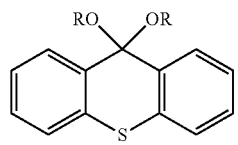

in which R=methyl, ethyl or propyl and wherein one or both of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio.

In one embodiment, one of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio, and the other aromatic ring is unsubstituted. For example, the one ring may be substituted with a single substituent selected from hydroxy, alkoxy, benzyloxy, alkylcarbonate, hydroxyalkyl, acetal, ester, oxyacetic acid and esters thereof, aryloxy and arylthio, or may be substituted with two substituents independently selected from hydroxy, alkoxy, benzyloxy, alkylcarbonate, hydroxyalkyl, acetal, ester, oxyacetic acid and esters thereof, aryloxy and arylthio, or may be substituted with three substituents independently selected from hydroxy, alkoxy, benzyloxy, alkylcarbonate, hydroxyalkyl, acetal, ester, oxyacetic acid and esters thereof, aryloxy and arylthio, or may be substituted with four substituents independently selected from hydroxy, alkoxy, benzyloxy, alkylcarbonate, hydroxyalkyl, acetal, ester, oxyacetic acid and esters thereof, aryloxy and arylthio.

In another embodiment, each of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio. For example, each of the rings may be substituted with a single substituent independently selected from hydroxy, alkoxy, benzyloxy, alkylcarbonate, hydroxyalkyl, acetal, ester, oxyacetic acid and esters thereof, aryloxy and arylthio, or one of the rings may be substituted with two substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio, or one of the rings may be substituted with three substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio or one of the rings is substituted with four substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with a single substituent selected from hydroxy, alkoxy, benzyloxy, alkylcarbonate, hydroxyalkyl, acetal, ester, oxyacetic acid and esters thereof, aryloxy and arylthio.

In the compounds of the invention alkoxy may be a C1-4 alkoxy, for example methoxy or t-butoxy. In some examples, alkoxy may be selected from the group consisting of dimethoxy, trimethoxy, ethoxy, diethoxy, triethoxy, propoxy, dipropoxy, tripropoxy, t-butoxy, di-t-butoxy, tri-t-butoxy. In some examples, the compounds of the invention have more than one methoxy substituent on the aromatic rings. In some examples, the compounds of the invention have a methoxy substituent on each aromatic ring. In some examples, the compounds of the invention have two methoxy substituents on one of the aromatic rings. In some examples, the compounds of the invention do not include 2-methoxy-9H-thioxanthen-9-one, 3,6-dimethoxy-9H-thioxanthen-9-one or any 1,3-dioxolane, 1,3-dioxane, 1,3 dioxepane, 1,3-dioxocane or 1,3-dioxonane derivatives thereof falling within the scope of Formula (I).

In the compounds of the invention hydroxyalkyl may be a hydroxy (C1-4) alkyl group, for example 2-hydroxyisopropyl.

In the compounds of the invention alkylcarbonate may be a C1-4 alkylcarbonate, for example t-butoxycarbonate.

In the compounds of the invention ester may be a C1-4 alkyl acid ester, for example acetic acid ester (acetate) or an ester of trifluoromethanesulfonic acid. In some examples, the ester may be an orthoester in which adjacent carbon atoms of the ring are each bonded to a respective oxygen atom and therewith form a 5- or 6-membered cyclic orthoester. The cyclic orthoester may be derived from trimethyl, triethyl or tripropyl orthoformate, for example triisopropyl orthoformate. For example in the case of trimethyl orthoformate, the resultant cyclic orthoester will be a 2-methoxybenzo[1,3]dioxole. In other examples, the resultant cyclic orthoester may be a 2-isopropoxybenzo[1,3]dioxole.

In the compounds of the invention acetal may be a C1-4 alkoxyalkyl group, for example methoxymethyl or ethoxyethyl. In some examples, the acetal may be a cyclic acetal in which adjacent carbon atoms of the ring are each bonded to a respective oxygen atom and therewith form a 5- or 6-membered cyclic acetal.

In the compounds of the invention benzyloxy may be a benzyloxy group comprising a substituted or unsubstituted benzyl group. The substituents may be selected from the group consisting of C1-6 alkyl for example methyl or ethyl, hydroxy, alkoxy, alkylcarbonate, acetal and ester.

In the compounds of the invention oxyacetic acid and esters thereof, may be oxyacetic acid or an ester thereof, for example an oxyacetic acid ester in which the esterifying group is selected from methyl, ethyl, n-propyl, iso-propyl, n-butyl, sec-butyl, t-butyl, isonorbonyl, 2-methyl-2-adamantyl, 3-tetrahydrofuranyl 3-oxocyclohexyl, γ-butyrolactone-3-yl, mevalonic lactone, γ-butyrolactone-2-yl, 3-methyl-γ-butyrolactone-3-yl, 2-tetrahydropyranyl, 2-tetrahydrofuranyl, 2,3-propylcarbonate-1-yl, a vinyl ether addition product such as ethoxyethyl, methoxy ethoxy ethyl or acetoxy ethoxy ethyl.

In the compounds of the invention, aryloxy may be a C5 or C6 aryloxy, for example phenoxy, which may be substituted. In the compounds of the invention, arylthio may be a C5 or C6 arylthio, for example phenylthio, which may be substituted. The substituents may be selected from the group consisting of C1-6 alkyl, for example methyl or ethyl, hydroxy, alkoxy, alkylcarbonate, acetal and ester.

In some embodiments of the invention, all of the substituents on the aromatic rings may be the same.

In some embodiments of the invention, the 1,3-dioxolane ring may be unsubstituted. In some embodiments of the invention, the 1,3-dioxolane ring may be substituted with one or more substituent selected from alkyl, cycloalkyl, chloroalkyl, aryl or vinyl in any substitution pattern. In some examples, (chloro)alkyl comprises C1-6 (chloro)alkyl, for example (chloro)methyl, (chloro)ethyl, (chloro)propyl, and also comprises (chloro)cycloalkyl in which two substituents on the 1,3-dioxolane ring may be joined to form a cyclic group, for example a 5- or 6-membered carbocycle fused to the 1,3-dioxolane ring. In some examples, the 1,3-dioxolane ring may be substituted with one or more C1-6 alkyl groups, for example two or more C1-6 alkyl groups. For example, the 1,3-dioxolane ring may be substituted with geminal or vicinal C1-6 alkyl groups in any substitution pattern, for example geminal or vicinal methyl groups. In some examples, the 1,3-dioxolane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

In some embodiments of the invention, the 1,3-dioxane ring may be unsubstituted. In some embodiments of the invention, the 1,3-dioxane ring may be substituted with one or more substituent selected from alkyl, cycloalkyl, chloroalkyl, aryl or vinyl in any substitution pattern. In some examples, (chloro)alkyl comprises C1-6 (chloro)alkyl, for example (chloro)methyl, (chloro)ethyl, (chloro)propyl, and also comprises (chloro)cycloalkyl in which two substituents on the 1,3-dioxane ring may be joined to form a cyclic group, for example a 5- or 6-membered carbocycle fused to the 1,3-dioxane ring. In some examples, the 1,3-dioxane ring may be substituted with one or more C1-6 alkyl groups, for example two or more C1-6 alkyl groups in any substitution pattern. For example, the 1,3-dioxane ring may be substituted with geminal or vicinal C1-6 alkyl groups, for example geminal or vicinal methyl groups. In some examples, the 1,3-dioxane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

In some embodiments of the invention, the 1,3-dioxepane ring may be unsubstituted. In some embodiments of the invention, the 1,3-dioxepane ring may be substituted with one or more substituent selected from alkyl, cycloalkyl, chloroalkyl, aryl or vinyl in any substitution pattern. In some examples, (chloro)alkyl comprises C1-6 (chloro)alkyl, for example (chloro)methyl, (chloro)ethyl, (chloro)propyl, and also comprises (chloro)cycloalkyl in which two substituents on the 1,3-dioxepane ring may be joined to form a cyclic group, for example a 5- or 6-membered carbocycle fused to the 1,3-dioxepane ring. In some examples, the 1,3-dioxepane ring may be substituted with one or more C1-6 alkyl groups, for example two or more C1-6 alkyl groups in any substitution pattern. For example, the 1,3-dioxepane ring may be substituted with geminal or vicinal C1-6 alkyl groups, for example geminal or vicinal methyl groups. In some examples, the 1,3-dioxepane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

In some embodiments of the invention, the 1,3-dioxocane ring may be unsubstituted. In some embodiments of the invention, the 1,3-dioxocane ring may be substituted with one or more substituent selected from alkyl, cycloalkyl, chloroalkyl, aryl or vinyl in any substitution pattern. In some examples, (chloro)alkyl comprises C1-6 (chloro)alkyl, for example (chloro)methyl, (chloro)ethyl, (chloro)propyl, and also comprises (chloro)cycloalkyl in which two substituents on the 1,3-dioxocane ring may be joined to form a cyclic group, for example a 5- or 6-membered carbocycle fused to the 1,3-dioxocane ring. In some examples, the 1,3-dioxocane ring may be substituted with one or more C1-6 alkyl groups, for example two or more C1-6 alkyl groups in any substitution pattern. For example, the 1,3-dioxocane ring may be substituted with geminal or vicinal C1-6 alkyl groups, for example geminal or vicinal methyl groups. In some examples, the 1,3-dioxocane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

In some embodiments of the invention, the 1,3-dioxonane ring may be unsubstituted. In some embodiments of the invention, the 1,3-dioxonane ring may be substituted with one or more substituent selected from alkyl, cycloalkyl, chloroalkyl, aryl or vinyl in any substitution pattern. In some examples, (chloro)alkyl comprises C1-6 (chloro)alkyl, for example (chloro)methyl, (chloro)ethyl, (chloro)propyl, and also comprises (chloro)cycloalkyl in which two substituents on the 1,3-dioxonane ring may be joined to form a cyclic group, for example a 5- or 6-membered carbocycle fused to the 1,3-dioxonane ring. In some examples, the 1,3-dioxonane ring may be substituted with one or more C1-6 alkyl groups, for example two or more C1-6 alkyl groups in any substitution pattern. For example, the 1,3-dioxonane ring may be substituted with geminal or vicinal C1-6 alkyl groups, for example geminal or vicinal methyl groups. In some examples, the 1,3-dioxonane ring may be substituted with one, two, three or four C1-6 alkyl groups, for example one, two, three or four methyl groups. It will be understood that in all of the above mentioned examples, C1-6 alkyl comprises methyl, ethyl, propyl, butyl, pentyl and hexyl, and all regioisomers thereof.

Compounds of the invention may have good solubility in aqueous media before and after deprotection. This may be characterized by reference to the octanol-water partition coefficient which may be calculated by various means.

For example, preferred compounds of the invention have a calculated log P (C log P) or mi log P as measured using the Molinspiration cheminformatics software, of less than 4.5, preferably less than 4.0. In other cases, the compounds of the invention may have improved solubility after deprotection.

The present invention also relates to the deprotected and deblocked form of the compounds of formula I or Ia in which the ketal, e.g. the diethyl ketal, the dipropyl ketal, the 1,3 dioxolane ketone blocking group or the 1,3-dioxane ketone blocking group or the 1,3-dioxepane ketone blocking group or the 1,3-dioxocane blocking group or the 1,3-dioxonane blocking group has been removed, and which have the formula II

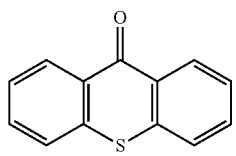

wherein one or both of the aromatic rings is substituted with at least one substituent independently selected from hydroxy, alkoxy, benzyloxy, hydroxyalkyl, oxyacetic acid, aryloxy and arylthio, and the compound is obtainable by reacting the compound of formula I or Ia in the presence of an acid, or in the presence of an acid and heat.

The compound of formula II may be obtainable by reacting the compound of formula I or Ia in the presence of an acid and heat. The acid and heat treatments may be simultaneous or may be subsequent. For example, the compound of formula II may be obtainable by firstly reacting the compound of formula I or Ia in the presence of an acid, followed by a subsequent heat treatment.

Examples of compounds of Formula (I), (Ia) and Formula (II) of the invention are as follows in Table 1, with selected compounds and their respective mi log P values shown in Table 2:

TABLE 1

| Structure | Name |
| --- | --- |
| 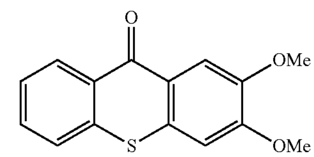 [SMILES: COc1cc2sc3ccccc3c(=O)c2cc1OC] | 2,3-dimethoxy-9H-thioxanthen-9-one |
| 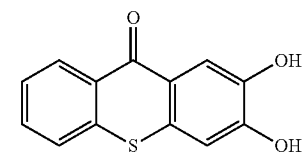 [SMILES: O=c1c2ccccc2sc2cc(O)c(O)cc12] | 2,3-dihydroxy-9H-thioxanthen-9-one |
| 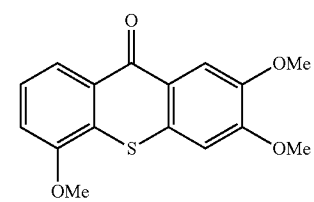 [SMILES: COc1cc2sc3c(OC)cccc3c(=O)c2cc1OC] | 2,3,5-trimethoxy-9H-thioxanthen-9-one |
| 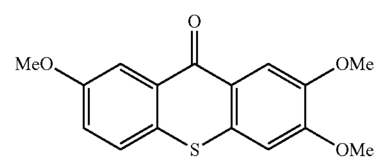 [SMILES: COc1ccc2sc3cc(OC)c(OC)cc3c(=O)c2c1] | 2,3,7-trimethoxy-9H-thioxanthen-9-one |
| 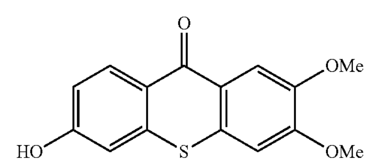 [SMILES: COc1cc2sc3cc(O)ccc3c(=O)c2cc1OC] | 1,5,6-trihydroxy-9H-thioxanthen-9-one |
| 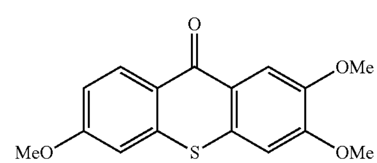 [SMILES: COc1ccc2c(=O)c3cc(OC)c(OC)cc3sc2c1] | 1,5,6-trimethoxy-9H-thioxanthen-9-one |
| 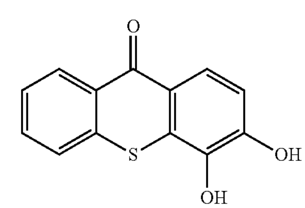 [SMILES: O=c1c2ccccc2sc2c(O)c(O)ccc12] | 3,4-dihydroxy-9H-thioxanthen-9-one |
| 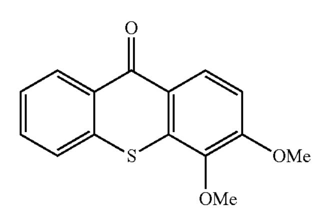 [SMILES: COc1ccc2c(=O)c3ccccc3sc2c1OC] | 3,4-dimethoxy-9H-thioxanthen-9-one |

TABLE 1-continued

| Structure | Name |
|---|---|
| 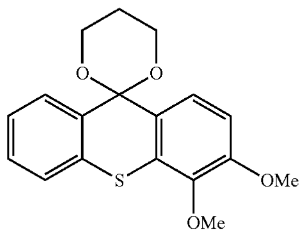 [SMILES: COc1ccc2c(c1OC)Sc1ccccc1C21OCCCO1] | 3',4'-dimethoxyspiro[1,3-dioxane-2,9'-thioxanthene] |
| 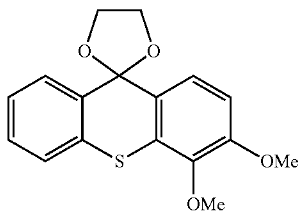 [SMILES: COc1ccc2c(c1OC)Sc1ccccc1C21OCCO1] | 3',4'-dimethoxyspiro[1,3-dioxolane-2,9'-thioxanthene] |
| 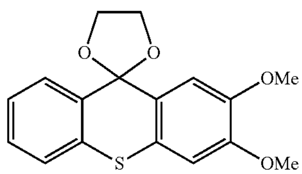 [SMILES: COc1cc2c(cc1OC)C1(OCCO1)c1ccccc1S2] | 2',3'-dimethoxyspiro[(1.3)-dioxolane-2,9'-thioxanthene] |
| 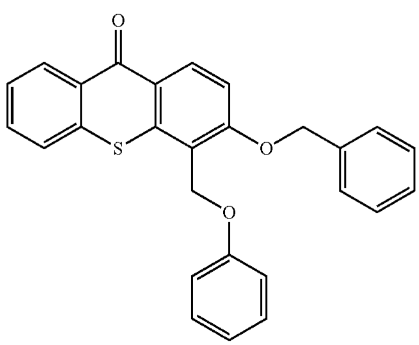 [SMILES: O=c1c2ccccc2sc2c(COc3ccccc3)c(OCc3ccccc3)ccc12] | 3,4-bis(benzyloxy)-9H-thioxanthen-9-one |
| 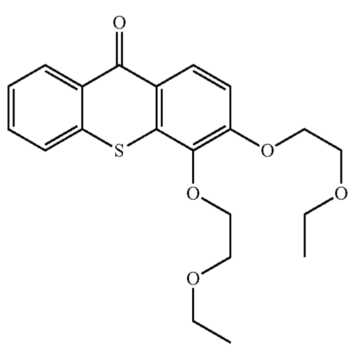 [SMILES: CCOCCOc1ccc2c(=O)c3ccccc3sc2c1OCCOCC] | 3,4-bis(1-ethoxyethyl)-9H-thioxanthen-9-one |
| 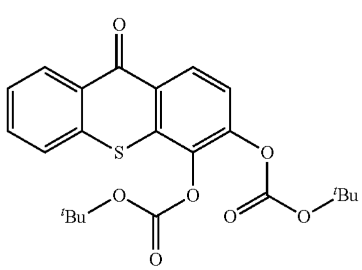 [SMILES: CC(C)(C)OC(=O)Oc1ccc2c(=O)c3ccccc3sc2c1OC(=O)OC(C)(C)C] | di-t-butyl (9-thioxo-9H-thioxanthene-3,4-diyl) dicarbonate |
| | methane; 2'-methoxy-5,6-dimethyl-spiro[1,3-dioxepane-2,6'-thiochromeno[3,2-g][1,3]benzodioxole] |
| | 2-methoxythiochromeno[3,2-g][1,3]benzodioxol-6-one |
| | 2'-methoxyspiro[1,3-dioxane-2,6'-thiochromeno[3,2-g][1,3]benzodioxole] |
| | 2'-methoxyspiro[1,3-dioxepane-2,6'-thiochromeno[2,3-g][1,3]benzodioxole] |
| | 2'-methoxy-5,5-dimethyl-spiro[1,3-dioxane-2,6'-thiochromeno[2,3-e][1,3]benzodioxole], |

TABLE 1-continued

| Structure | Name |
|---|---|
| 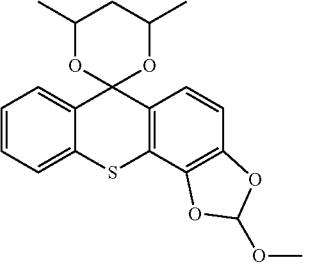 [SMILES: COC1Oc2ccc3c(c2O1)Sc1ccccc1C31OC(C)CC(C)O1] | 2'-methoxy-4,6-dimethyl-spiro[1,3-dioxane-2,6'-thiochromeno[3,2-g][1,3]benzodioxole], |
| 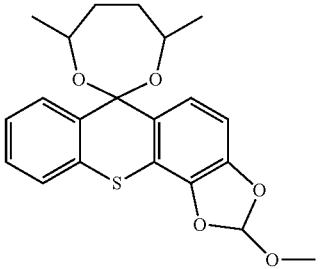 [SMILES: COC1Oc2ccc3c(c2O1)Sc1ccccc1C31OC(C)CCC(C)O1] | 2'-methoxy-4,7-dimethyl-spiro[1,3-dioxepane-2,6'-thiochromeno[2,3-e][1,3]benzodioxole] |
| 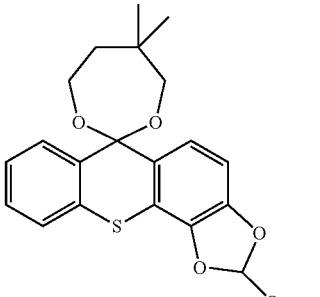 | 2'-methoxy-5,5-dimethyl-spiro[1,3-dioxepane-2,6'-thiochromeno[2,3-e][1,3]benzodioxole] |
| 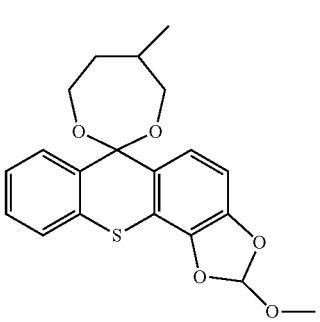 [SMILES: COC1Oc2ccc3c(c2O1)Sc1ccccc1C31OCCC(C)CO1] | 2'-methoxy-5-methyl-spiro[1,3-dioxepane-2,6'-thiochromeno[2,3-e][1,3]benzodioxole] |
| 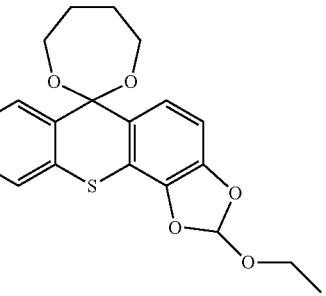 | 2'-ethoxyspiro[1,3-dioxepane-2,6'-thiochromeno[2,3-e][1,3]benzodioxole] |

TABLE 1-continued

| Structure | Name |
|---|---|
| 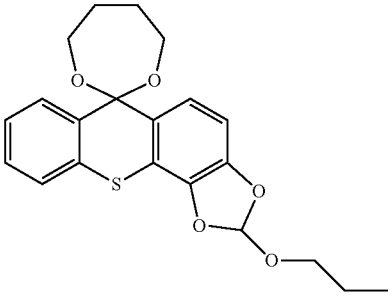 [SMILES: CCCOC1Oc2ccc3c(c2O1)Sc1ccccc1C31OCCCCO1] | 2'-propoxyspiro[1,3-dioxepane-2,6'-thiochromeno[3,2-g][1,3]benzodioxole] |
| 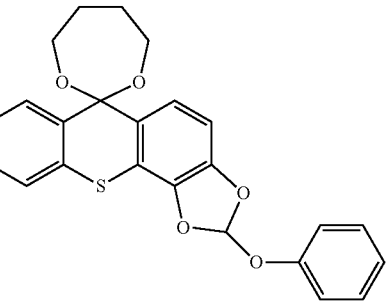 | 2'-phenoxyspiro[1,3-dioxepane-2,6'-thiochromeno[2,3-e][1,3]benzodioxole] |
| 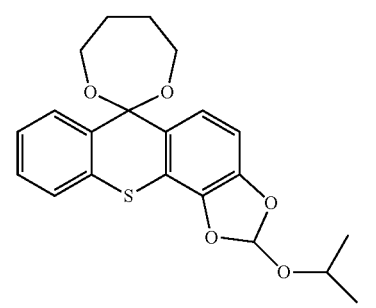 [SMILES: CC(C)OC1Oc2ccc3c(c2O1)Sc1ccccc1C31OCCCCO1] | 2'-isopropoxyspiro[1,3-dioxepane-2,6'-thiochromeno[2,3-e][1,3]benzodioxole] |
| 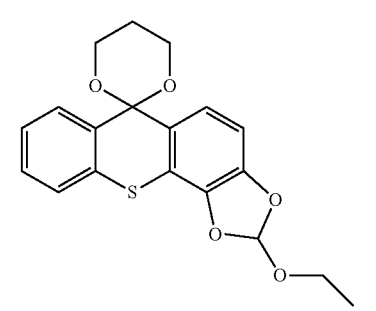 [SMILES: CCOC1Oc2ccc3c(c2O1)Sc1ccccc1C31OCCCO1] | 2'-ethoxyspiro[1,3-dioxane-2,6'-thiochromeno[3,2-g][1,3]benzodioxole], |
| 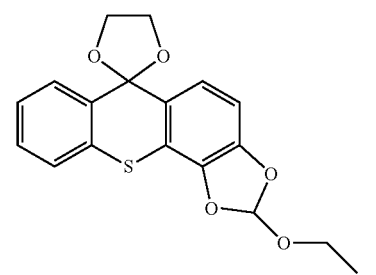 [SMILES: CCOC1Oc2ccc3c(c2O1)Sc1ccccc1C31OCCO1] | 2'-ethoxyspiro[1,3-dioxolane-2,6'-thiochromeno[2,3-e][1,3]benzodioxole] |

TABLE 1-continued

| Structure | Name |
|---|---|
| | 2'-propoxyspiro[1,3-dioxane-2,6'-thiochromeno[3,2-g][1,3]benzodioxole] |
| | 2'-propoxyspiro[1,3-dioxolane-2,6'-thiochromeno[2,3-e][1,3]benzodioxole] |
| | 2'-isopropoxyspiro[1,3-dioxane-2,6'-thiochromeno[2,3-e][1,3]benzodioxole], |
| | 2'-isopropoxyspiro[1,3-dioxolane-2,6'-thiochromeno[3,2-g][1,3]benzodioxole] |
| | 2'-methoxyspiro[1,3-dioxane-2,6'-thiochromeno[2,3-e][1,3]benzodioxole], |
| 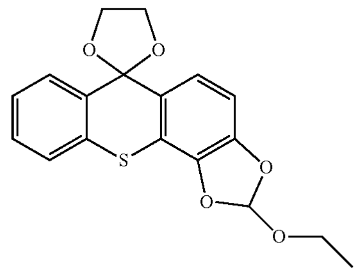 [SMILES: CCOC1Oc2ccc3c(c2O1)Sc1ccccc1C31OCCO1] | 2'-methoxyspiro[1,3-dioxolane-2,6'-thiochromeno[2,3-e][1,3]benzodioxole] |
| 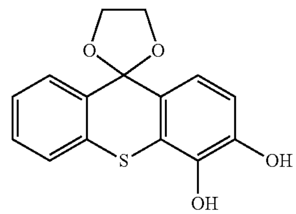 [SMILES: Oc1ccc2c(c1O)Sc1ccccc1C21OCCO1] | spiro[1,3-dioxolane-2,9'-thioxanthene]-3',4'-diol |
| 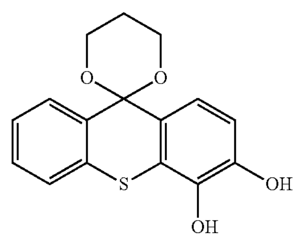 [SMILES: Oc1ccc2c(c1O)Sc1ccccc1C21OCCCO1] | spiro[1,3-dioxane-2,9'-thioxanthene]-3',4'-diol, |
| 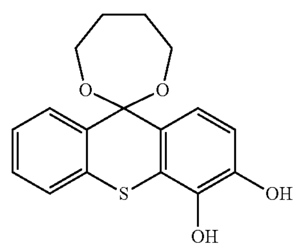 [SMILES: Oc1ccc2c(c1O)Sc1ccccc1C21OCCCCO1] | spiro[1,3-dioxepane-2,9'-thioxanthene]-3',4'-diol |
| 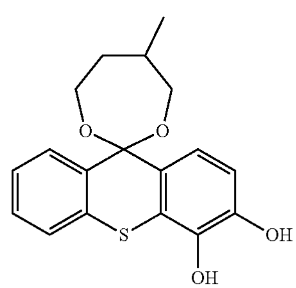 [SMILES: CC1CCOC2(OC1)c1ccccc1Sc1c2ccc(O)c1O] | 5-methylspiro[1,3-dioxepane-2,9'-thioxanthene]-3',4'-diol |
| 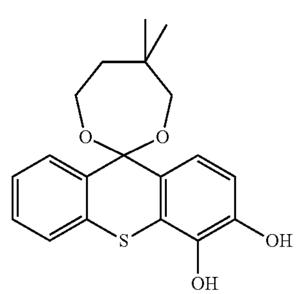 [SMILES: CC1(C)CCOC2(OC1)c1ccccc1Sc1c2ccc(O)c1O] | 5,5-dimethylspiro[1,3-dioxepane-2,9'-thioxanthene]-3',4'-diol |

TABLE 1-continued

| Structure | Name |
|---|---|
|  | 2-ethoxythiochromeno[2,3-e][1,3]benzodioxol-6-one |
| 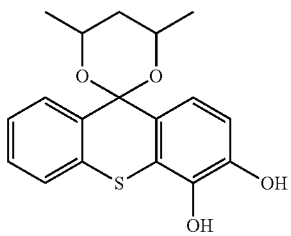 [SMILES: CC1CC(C)OC2(O1)c1ccccc1Sc1c2ccc(O)c1O] | 3',4'-dimethoxy-4,6-dimethyl-spiro[1,3-dioxane-2,9'-thioxanthene] |
| 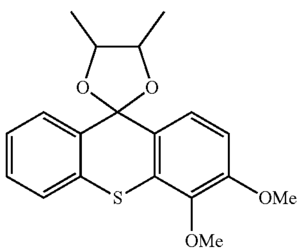 [SMILES: COc1ccc2c(c1OC)Sc1ccccc1C21OC(C)C(C)O1] | 3',4'-dimethoxy-4,5-dimethyl-spiro[1,3-dioxolane-2,9'-thioxanthene] |
| 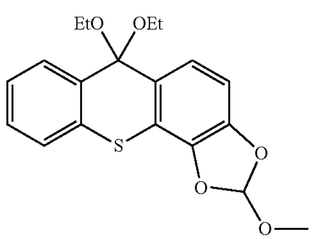 [SMILES: CCOC1(OCC)c2ccccc2Sc2c1ccc1c2OC(OC)O1] | 6,6-diethoxy-2-methoxy-thiochromeno[2,3-e][1,3]benzodioxole |
| 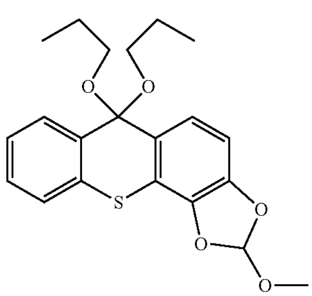 [SMILES: CCCOC1(OCCC)c2ccccc2Sc2c1ccc1c2OC(OC)O1] | 2-methoxy-6,6-dipropoxy-thiochromeno[3,2-g][1,3]benzodioxole |
| 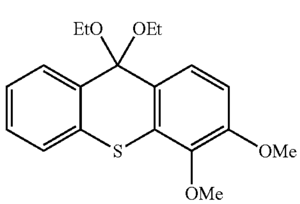 [SMILES: CCOC1(OCC)c2ccccc2Sc2c1ccc(OC)c2OC] | 9,9-diethoxy-3,4-dimethoxy-thioxanthene |

TABLE 2

| Compound | miLogP value |
|---|---|
| 2,3-dimethoxy-9H-thioxanthen-9-one | 3.83 |
| 2,3-dihydroxy-9H-thioxanthen-9-one | 3.22 |
| 2,3,5-trimethoxy-9H-thioxanthen-9-one | 3.84 |
| 2,3,7-trimethoxy-9H-thioxanthen-9-one | 3.87 |
| 1,5,6-trihydroxy-9H-thioxanthen-9-one | 2.95 |
| 1,5,6-trimethoxy-9H-thioxanthen-9-one | 4.04 |
| 3,4-dihydroxy-9H-thioxanthen-9-one | 3.45 |
| 3,4-dimethoxy-9H-thioxanthen-9-one | 4.03 |
| 3',4'-dimethoxyspiro[1,3-dioxane-2,9'-thioxanthene] | 3.58 |
| 2',3'-dimethoxyspiro[(1.3)-dioxolane-2,9'-thioxanthene] | 3.11 |
| 3,4-bis(benzyloxy)-9H-thioxanthen-9-one | 7.22 |
| 3,4-bis(1-ethoxyethyl)-9H-thioxanthen-9-one | 5.45 |
| di-t-butyl (9-thioxo-9H-thioxanthene-3,4-diyl)dicarbonate | 6.10 |
| methane;2'-methoxy-5,6-dimethyl-spiro[1,3-dioxepane-2,6'-thiochromeno[3,2-g][1,3]benzodioxole] | 4.80 |
| 2-methoxythiochromeno[3,2-g][1,3]benzodioxol-6-one | 4.04 |
| 2'-methoxyspiro[1,3-dioxane-2,6'-thiochromeno[3,2-g][1,3]benzodioxole] | 3.58 |
| 2'-methoxyspiro[1,3-dioxepane-2,6'-thiochromeno[2,3-g][1,3]benzodioxole] | 3.85 |
| 2'-methoxy-5,5-dimethyl-spiro[1,3-dioxane-2,6'-thiochromeno[2,3-e][1,3]benzodioxole] | 4.47 |
| 2'-methoxy-4,6-dimethyl-spiro[1,3-dioxane-2,6'-thiochromeno[3,2-g][1,3]benzodioxole] | 4.31 |
| 2'-methoxy-4,7-dimethyl-spiro[1,3-dioxepane-2,6'-thiochromeno[2,3-e][1,3]benzodioxole] | 4.58 |
| 2'-methoxy-5,5-dimethyl-spiro[1,3-dioxepane-2,6'-thiochromeno[2,3-e][1,3]benzodioxole] | 4.74 |
| 2'-methoxy-5-methyl-spiro[1,3-dioxepane-2,6'-thiochromeno[2,3-e][1,3]benzodioxole] | 4.33 |

Compositions and Photoinitiated Methods

In a second aspect, the present invention relates to a composition comprising:
  a compound of formula I or Ia as defined above; and
  a chemically transformable substrate;
  wherein the compound of formula I or Ia is a precursor of a reactive derivative of formula II:

$$\text{(II)}$$

wherein one or both of the aromatic rings is substituted with at least one substituent independently selected from hydroxy, alkoxy, benzyloxy, alkylcarbonate, hydroxyalkyl, acetal, ester, oxyacetic acid and esters thereof, aryloxy and arylthio, the compound of formula II being obtainable by reacting the compound of formula I or Ia in the presence of an acid;
  and further wherein the transformable substrate is capable of being transformed in the presence of the compound of formula II by a direct photoinitiated reaction or an indirect photoinitiated reaction.

In the composition of the second aspect, the compound of formula I or Ia may be a precursor of a reactive derivative of a compound of formula II having any substitution pattern as described above.

The compound of formula II may be obtainable by reacting the compound of formula I or Ia in the presence of an acid and heat. The acid and heat treatments may be simultaneous or may be subsequent. For example, the compound of formula II may be obtainable by firstly reacting the compound of formula I or Ia in the presence of an acid, followed by a subsequent heat treatment.

The compositions of the invention may be used in photoinitiated methods. Thus, in a third aspect of the invention, there is provided a photoinitiated method which comprises:
(a) forming a layer of a composition of the second aspect of the invention on a support;
(b) applying an acid, or generating an acid in situ, in selected regions of the layer and permitting the acid to react with the compound of formula I or Ia and form the reactive derivative of formula II in said selected regions of the layer;
(c) exposing the layer with the reactive derivative present in said selected regions to electromagnetic radiation of a wavelength or energy suitable to generate a reactive species from the compound of formula II; and
(d) permitting the reactive species directly or indirectly to cause transformation of the transformable substrate.

In some embodiments, permitting the acid to react with the compound of formula I or Ia and form the reactive derivative of formula II may comprise application of heat. The application of heat may be simultaneous with the applying of an acid or generating an acid in situ, or it may be subsequent to this step.

In some embodiments, the method may further comprise performing a pre-transformation and/or a post-transformation heat treatment. In other words, following c) above in which the layer with the reactive derivative is exposed to electromagnetic radiation, there may be a heat treatment to enable reaction of acid present with the transformable substrate. Similarly, following d) above in which the reactive species causes transformation of the transformable substrate, there may be a heat treatment, to initiate curing in the remaining transformed substrate.

The reactive species may, for example, be a free radical species or an energetically excited form of compound of formula II.

In one embodiment, an acid may be applied to selected regions of the layer to react with the compound of formula I or Ia and form the reactive derivative of formula II in said selected regions of the layer. The acid may, for example, be applied by spraying or ink jet printing.

In another embodiment, an acid generator is incorporated in the composition applied to the substrate. Preferred is a photoacid generator (PAG), but thermal acid generators (TAG) are also operable. The acid generator is a species which is capable of generating acid in response to an external stimulus, thereby allowing acid to be generated in situ, which acid reacts with the compound of formula I or Ia to form the reactive derivative of formula II in selected regions of the layer where the acid has been generated. Although presently less preferred, the acid generator may be applied to the layer subsequent to the formation of the layer, by for example spraying or ink jet printing.

In some examples, the application of acid or generation of acid in situ is followed by a heat treatment step, in order to permit the acid to sufficiently react with the compound of formula I or Ia and form the reactive derivative of formula II in all selected regions of the layer. The heat treatment step may be performed regardless of whether the acid was applied externally, or generated by a photoacid generator or a thermal acid generator. The temperature and duration of the heat treatment may vary depending, for example, on the concentration and strength of an acid applied externally, or on the intensity and duration of an exposure to electromagnetic radiation in the case of a photoacid generator.

The reactive derivative of formula II is formed in the selected regions of the layer in a first stage of the method. In the subsequent stage, exposure to electromagnetic radiation of a suitable wavelength causes a reactive species to be generated from the compound of formula II. In the case that the first stage is carried out photochemically using a PAG, the wavelength of the electromagnetic radiation used in the subsequent stage is different to the wavelength of the electromagnetic radiation used in the first stage and is selected to avoid the generation of further acid from the PAG. This allows the application of electromagnetic radiation in the second stage to be conducted at high energy as a flood radiation which does not need to be carried out in an imagewise fashion.

As used herein, a direct photoinitiated reaction is one in which the reactive species which is generated from the compound of formula II directly causes transformation of the transformable substrate. This may, for example, occur where the reactive species directly initiates polymerization of a polymerisable monomer.

An indirect photoinitiated reaction is one in which the reactive species which is generated from the compound of formula II indirectly causes transformation of the reactive substrate. This may, for example, occur where the reactive species interacts with a second photoinitiator or synergist by transferring its energy or electron(s) to the other species which then initiates or causes transformation of the transformable substrate. Another example of an indirect photoinitiated reaction is one in which the reactive species photosensitizes a photoacid generator to generate acid which is capable of causing transformation of a polymerizable substrate via cationic polymerization, or which is capable of removing acid labile protecting groups of a protected polymer to render the polymer soluble in a suitable developer. In such a method, generating acid capable of causing transformation of a polymerizable substrate may be performed with the application of heat. In some examples, there may also be a heat treatment following dissolution and wash-off of solubilized polymer to permit cure of the remaining composition.

The compositions of the invention have particular suitability as photoresist compositions. A layer of such a composition on a substrate, such as may be used in the method of the third aspect of the invention, is termed a photoresist. Another aspect of the present invention is a photoresist layer formed of the composition of the second aspect of the invention on a substrate.

The transformable substrate may be a polymerisable substrate, for example a cationically polymerisable substrate or a free radical promoted polymerisable substrate or a substrate containing acid labile protecting groups on a protected polymer which can be removed by acid to render the polymer soluble in a suitable developer.

The cationic polymerizable compounds may be monomers, oligomers and/or prepolymers. These monomers, oligomers and/or prepolymers may possess different degrees of functionality. A mixture including combinations of mono-, di-, tri- and higher functional monomers, oligomers and/or prepolymers may be used.

In a preferred embodiment, the monomer, oligomer or prepolymer includes at least one epoxy, at least one vinyl ether, or at least one oxetane group as polymerizable group.

Examples of monomers, oligomers or prepolymers containing at least one epoxide group include, epichlorohydrin-bisphenol S based epoxides, epoxidized styrenics and more epichlorohydrin-bisphenol F and A based epoxides and epoxidized novolacs, alicyclic polyepoxide, polyglycidyl ester of polybasic acid, polyglycidyl ether of polyol, polyglycidyl ether of polyoxyalkylene glycol, polyglycidyl ester of aromatic polyol, polyglycidyl ether of aromatic polyol, urethane polyepoxy compound, and polyepoxy polybutadiene cycloaliphatic epoxy compounds such as bis-(3,4-epoxycyclohexyl)-adipate, 3,4-epoxycyclohexylmethyl-3,4-epoxycyclohexane carboxylate, poly[(2-oxiranyl)-1,2-cyclohexanediol]-2-ethyl-2-(hydroxymethyl)-1,3-propanediol ether, 7-oxabicyclo[4.1.0]hept-3-ylmethyl 7-oxa-bicyclo[4.1.0]heptane-3-carboxylate; ether derivatives including diol derivatives such as 3-(bis(glycidyloxymethyl)methoxy)-1,2-propane diol, limonene oxide, 2-biphenyl glycidyl ether 1,4-butanediol diglycidylether and neopentyl glycol diglycidylether; glycidyl ethers such as n-butyl glycidyl ether, distilled butyl glycidyl ether, 2-ethylhexyl glycidyl ether, C8-C10 aliphatic glycidyl ether, C12-C14 aliphatic glycidyl ether, o-cresyl glycidyl ether, p-tertiary butyl phenyl glycidyl ether, nonyl phenyl glycidyl ether, phenyl glycidyl ether, cyclohexanedimethanol diglycidyl ether, polypropylene glycol diglycidyl ether, poly glycol diglycidyl ether, dibromo neopentyl glycol diglycidyl ether, trimethylolpropane triglycidyl ether, castor oil triglycidyl ether, propoxylated glycerin triglycidyl ether, sorbitol polyglycidyl ether, glycidyl ester of neodecanoic acid; and glycidyl amines such as epoxidized meta-xylene diamine.

Examples of monomers, oligomers or prepolymers containing at least one vinyl ether group include ethyl vinyl ether, n-butyl vinyl ether, isobutyl vinyl ether, octadecyl vinyl ether, cyclohexyl vinyl ether, butanediol divinyl ether, hydroxyl butyl vinyl ether, cyclohexane dimethanol monovinyl ether, phenyl vinyl ether, p-methylphenyl vinyl ether, p-methoxyphenyl vinyl ether, a-methylphenyl vinyl ether, b-methylisobutyl vinyl ether and b-chloroisobutyl vinyl ether, diethyleneglycol divinyl ether, triethylene glycol divinyl ether, n-propyl vinyl ether, isopropyl vinyl ether, dodecyl vinyl ether, diethylene glycol monovinyl ether, cyclohexanedimethanol divinyl ether, 4-(vinyloxy)butyl benzoate, bis[4-(vinyl oxy)butyl]adipate, bis[4-(vinyl oxy)butyl] succinate, 4-(vinyloxy methyl)cyclohexylmethyl benzoate, bis[4-(vinyloxy)butyl]isophthalate, bis[4-(vinyloxymethyl) cyclohexylmethyl]glutarate, tris[4-(vinyloxy)butyl]trimellitate,4-(vinyloxy)butyl steatite, bis[4-(vinyloxy)butyl] hexanediylbiscarbamate, bis[4-(vinyloxy)methyl] cyclohexyl]methyl]terephthalate, bis[4-(vinyloxy)methyl] cyclohexyl]methyl]isophthalate, bis[4-(vinyloxy)butyl](4-methyl-1,3-phenylene)-biscarbamate, bis[4-vinyloxy)butyl] (methylenedi-4,1-phenylene) biscarbamate and 3-amino-1-propane vinyl ether.

Examples of monomers, oligomers or prepolymers containing at least one oxetane group include 3,3'-oxybis(methylene)bis(3-ethyloxetane), 3-ethyl-3-hydroxymethyl-1-oxetane, the oligomeric mixture 1,4-bis [3-ethyl-3-oxetanyl methoxy)methyl]benzene, 3-ethyl-3-[(phenylmethoxy) methyl]-oxetane, 3-ethyl-3-[(2-ethylhexyloxy) methyl]oxetane and bis[1-Ethyl(3-oxetanyl)]methylether, 3-ethyl-[(triethoxysilyl propoxy)methyl]oxetane and 3,3-dimethyl-2(p-methoxy-phenyl)-oxetane.

The free radical polymerizable compounds may be monomers, oligomers and/or prepolymers. These monomers, oligomers and/or prepolymers may possess different degrees of functionality. A mixture including combinations of mono-, di-, tri- and higher functional monomers, oligomers and/or prepolymers may be used.

In another preferred embodiment the monomer, oligomer or prepolymer includes at least one acrylate or at least one methacrylate group as polymerizable group.

Suitable free radical promoted polymerizable mono functional or polyfunctional monomers are: isoamyl acrylate, stearyl acrylate, lauryl acrylate, octyl acrylate, decyl acrylate, isoamylstyl acrylate, isostearyl acrylate, 2-ethylhexyl-diglycol acrylate, 2-hydroxybutyl acrylate, 2-acryloyloxyethylhexahydrophthalic acid, butoxyethyl acrylate, ethoxydiethylene glycol acrylate, methoxydiethylene glycol acrylate, methoxypolyethylene glycol acrylate, methoxypropylene glycol acrylate, phenoxyethyl acrylate, tetrahydrofurfuryl acrylate, isobornyl acrylate, 2-hydroxyethyl acrylate, 2-hydroxypropyl acrylate, 2-hydroxy-3-phenoxypropyl acrylate, vinyl ether 10 acrylate, 2-acryloyloxyethylsuccinic acid, 2-acryloyxyethylphthalic acid, 2-acryloxyethyl-2-hydroxyethyl-phthalic acid, lactone modified flexible acrylate, and t-butylcyclohexyl acrylate, triethylene glycol diacrylate, tetraethylene glycol diacrylate, polyethylene glycol diacrylate, dipropylene glycol diacrylate, tripropylene glycol diacrylate, polypropylene glycol diacrylate, 1,4-butanediol diacrylate, 1,6-hexanediol diacrylate, 1,9-nonanediol diacrylate, neopentyl glycol diacrylate, dimethylol-tricyclodecane diacrylate, bisphenol A EO (ethylene oxide) adduct diacrylate, bisphenol A PO (propylene oxide) adduct diacrylate, hydroxypivalate neopentyl glycol diacrylate, propoxylated neopentyl glycol diacrylate, alkoxylated dimethyloltricyclodecane diacrylate and polytetramethylene glycol diacrylate, trimethylolpropane triacrylate, EO modified trimethylolpropane triacrylate, tri (propylene glycol) triacrylate, caprolactone modified trimethylolpropane triacrylate, pentaerythritol triacrylate, pentaerithritol tetraacrylate, pentaerythritolethoxy tetraacrylate, dipentaerythritol hexaacrylate, ditrimethylolpropane tetraacrylate, glycerinpropoxy triacrylate, and caprolactam modified dipentaerythritol hexaacrylate, or an N-vinylamide such as, N-vinylcaprolactam or N-vinylformamide; or acrylamide or a substituted acrylamide, such as acryloylmorpholine.

Other suitable monofunctional acrylates include caprolactone acrylate, cyclic trimethylolpropane formal acrylate, ethoxylated nonyl phenol acrylate, isodecyl acrylate, isooctyl acrylate, octyldecyl acrylate, alkoxylated phenol acrylate, tridecyl acrylate and alkoxylated cyclohexanone dimethanol diacrylate.

Other suitable difunctional acrylates include alkoxylated cyclohexanone dimethanol diacrylate, alkoxylated hexanediol diacrylate, dioxane glycol diacrylate, dioxane glycol diacrylate, cyclohexanone dimethanol diacrylate, diethylene glycol diacrylate and neopentyl glycol diacrylate.

Other suitable trifunctional acrylates include propoxylated glycerine triacrylate and propoxylated trimethylolpropane triacrylate.

Other higher functional acrylates include di-trimethylolpropane tetraacrylate, dipentaerythritol pentaacrylate, ethoxylated pentaeryhtitol tetraacrylate, methoxylated glycol acrylates and acrylate esters.

Furthermore, methacrylates corresponding to the above-mentioned acrylates may be used with these acrylates.

Examples of polymerizable oligomers include epoxy acrylates, aliphatic urethane acrylates, aromatic urethane acrylates, polyester acrylates, and straight-chained acrylic oligomers.

Use of polymerizable substrates enables the formation of a negative photoresist in which the exposed portions or regions of the photoresist become insoluble to the photoresist developer via the polymerization reaction of the transformable substrate. In the case of the cationic polymerisable substrate, there may also be a heating step after the exposure to UV light, the so called post exposure bake (PEB) to complete the polymerisation reaction. The unexposed and unpolymerised portion can be dissolved and removed by a suitable photoresist developer. After the step using the developer, a patterned coating which is insoluble in the developer remains on the surface. Depending on the application for the photoresist, for example as permanent coating such as a solder mask or dielectric layer, further steps may be carried out to harden the coating, such as a curing step which may be performed by the application of heat and/or additional exposure to UV light.

In the case of the application of heat, this may be achieved for example by heating on a hot plate or by baking in a static or conveyorised hot air circulating oven, or by using a conveyorised infra-red oven. In the case of additional exposure to light, this can be done for example by passing the substrate under a lamp emitting UV light of a wavelength or wavelengths suitable for initiating further free radical polymerisation using a conveyor.

In the case of a temporary resist such as an etch or plate resist, the additional curing step is not usually required since it would make later removal of the resist more difficult.

In another embodiment, the transformable substrate may be a protected polymer, for example a polymer having polar groups protected by acid labile groups, the polymer, after removal of the acid labile groups, being soluble in a developing medium. Examples of suitable polymers protected by acid labile groups are described in, for example U.S. Pat. No. 4,491,628 A, the contents of which are incorporated herein by reference, and include poly (tert-butyloxycarbonyloxy-α-alkylstyrene), poly (p-tert-butyloxycarbonyloxy-α-methylstyrene), poly (tert-butyloxycarbonyloxystyrene), poly (p-tert-butyloxycarbonyloxy-styrene) and poly (tert-butyl vinylbenzoate), poly (tert-butylmethacrylate), or copolymers thereof. In such examples, the acid labile groups are tert-butyl esters, of pendent carboxylic groups of the polymer or tert-butylcarbonates of pendent phenols of the polymer. Other examples of suitable polymers protected by acid labile groups are described in U.S. Pat. Nos. 7,858,287 B2, 9,529,259 B2 and 6,136,499 A, the contents of which are incorporated herein by reference.

This embodiment enables the formation of a positive photoresist in which the exposed portion of the photoresist becomes soluble to the photoresist developer via deprotection of the polymer, and can thus be removed by the developer, while the unexposed portions of the photoresist remain insoluble to the photoresist developer. After the step using the developer, a patterned coating which is insoluble in the developer remains on the surface. Further steps may be carried out to harden the coating, such as a curing step which may be performed by the application of heat. An example of an application of a positive photoresist is in high resolution lithography.

In another embodiment the transformable substrate may be a protected dissolution accelerator, for example a dissolution inhibitor containing acid-labile groups which, after acid catalysed hydrolytic reactions produce materials which are dissolution accelerators. Examples of dissolution inhibitors containing acid-labile groups and their use are given in pp 223-227 of "Introduction to Microlithography ($2^{nd}$ edition) ISBN 0-8412-2848-5 and FIG. 85.

The composition may further comprise a quencher, also termed an acid diffusion controlling agent or a photodecomposable version thereof. Such compounds control diffusion, in a resist film, of an acid generated through exposure to light, thereby suppressing undesired chemical reaction in an unexposed area. The acid diffusion controlling agent may be a nitrogen-containing organic compound whose basicity does not change through light exposure or thermal treatment and is typically present in an amount of 0.005 to 5 wt. % of the composition. Examples of acid diffusion controlling agents are amines such as secondary lower aliphatic amines, tertiary lower aliphatic amines or the like such as: trimethylamine, diethylamine, di-n-propylamine, tri-n-propylamine, tripentylamine, diethanolamine, triethanolamine, quaternary ammonium compounds, trialkylammonium compounds amides, ureas, TBOC-blocked amines, and combinations of these and the like.

Examples of photodecomposable acid diffusion controlling agents include arylsulfonium or Iodonium salts containing anions, such as acetate, hydroxide, or sulfamate as well as those disclosed in U.S. Pat. No. 8,614,047 B2.

The composition may include further components known in the art such as crosslinking agents, colourants, inorganic mineral fillers, surface modifiers such as flow and debubbling agents, free radical scavengers, stabilisers, plasticisers, adhesion promoters.

More details of photoinitiated methods in which the compounds and compositions of the present invention may be used are described in WO 2011/086389 A1, the contents of which are hereby incorporated by reference in their entirety.

Further, the compounds and compositions may be used in the photosensitized chemically amplified resist (PSCAR) methods described in US2015241783 A1, US2016327869 A1, US2016357103 A1, "Photosensitized Chemically Amplified Resist™ (PSCAR™) 2.0 for high throughput and high resolution EUV lithography: Dual photosensitization of acid generation and quencher decomposition by flood exposure", S. Tagawa et al., Proc. of SPIE Vol. 10146, Advances in Patterning Materials and Processes XXXIV, 101460G (2017), "Super High Sensitivity Enhancement by Photo-Sensitized Chemically Amplified Resist (PS-CAR) Process," S. Tagawa et al., J. Photopolymer Science and Technology, 26(6), 825 (2013), and "High-resist sensitization by pattern and flood combination lithography," S. Nagahara et al., Proc. SPIE, 9048, 90481S (2014), all of which are incorporated by reference in their entirety for all purposes. The electromagnetic wave for patterning in the first stage can be EUV (13.5 nm), ArF (193 nm), KrF (248 nm) or electron beams for example. The electromagnetic radiation used in the second stage as flood radiation can be 365 nm, 375 nm, 385 nm, 395 nm, 405 nm, or 415 nm LEDs, or UV lamp which has wider wavelength distribution.

Synthesis of the Compounds of the Invention

The compounds of the invention of formula I may be synthesized by a variety of methods.

Compounds of formula I in which one or both of the rings of, for example, the spiro[(1,3)dioxolane-2,9'-thioxanthene] structure are substituted by hydroxy groups or hydroxyalkyl groups may be synthesized by first preparing the corresponding hydroxy or hydroxyalkyl substituted 9H-thioxanthen-9-one compound, and subsequently protecting the hydroxy groups with a suitable protecting group which can be subsequently removed. The protected structure is then reacted with ethylene glycol in order to protect the carbonyl group with a 1,3 dioxolane group or 1,3-propylene glycol to protect the carbonyl group with a 1,3-dioxane group, or 1,4-butanediol to protect the carbonyl group with a 1,3-dioxepane group, or 1,5-pentanediol to protect the carbonyl group with a 1,3-dioxocane group, or a 1,6-hexanediol to protect the carbonyl group with a 1,3-dioxonane group. Other glycols may also be used to produce substituted dioxolane or dioxane groups. The hydroxy protecting groups may then be removed to produce the, for example, hydroxy or hydroxyalkyl substituted spiro[(1,3)dioxolane-2,9'-thioxanthene]compounds.

The synthesis of the compounds of formula I in which one or both of the rings of a, for example, spiro[(1,3)dioxolane-2,9'-thioxanthene]structure are substituted by alkoxy groups may be synthesized by first preparing the corresponding alkoxy substituted 9H-thioxanthen-9-one compound.

The alkoxy substituted 9H-thioxanthen-9-one compound is reacted with Lawessons reagent (2,4-Bis(4-methoxyphenyl)-1,3,2,4-dithiadiphosphetane-2,4-dithione followed by reaction with ethylene glycol. This synthetic route is illustrated in the following specific reaction scheme:

Scheme 1

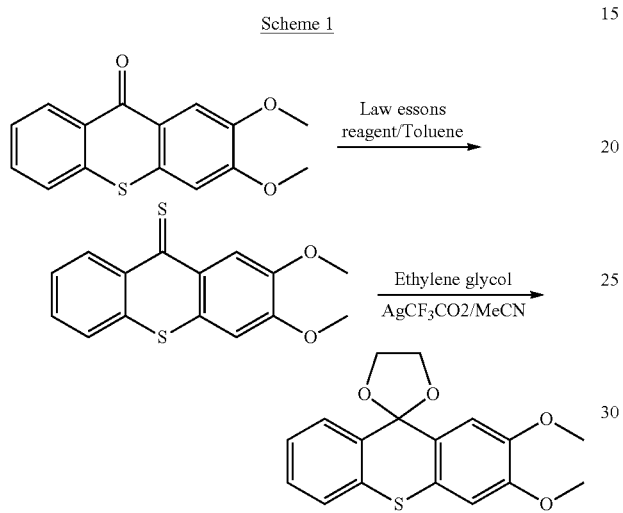

The alkoxy, hydroxy and hydroxyalkyl substituted 9H-thioxanthen-9-one precursors may be prepared by various synthetic routes.

In the case of hydroxyalkyl substituted 9H-thioxanthen-9-one precursors, these may be prepared from the corresponding alkyl substituted compound via bromination with a suitable brominating agent such as N-bromyl succinimide (NBS) followed by treatment with an alkali such as sodium hydroxide. This synthetic route is illustrated in the following specific reaction scheme:

Scheme 2

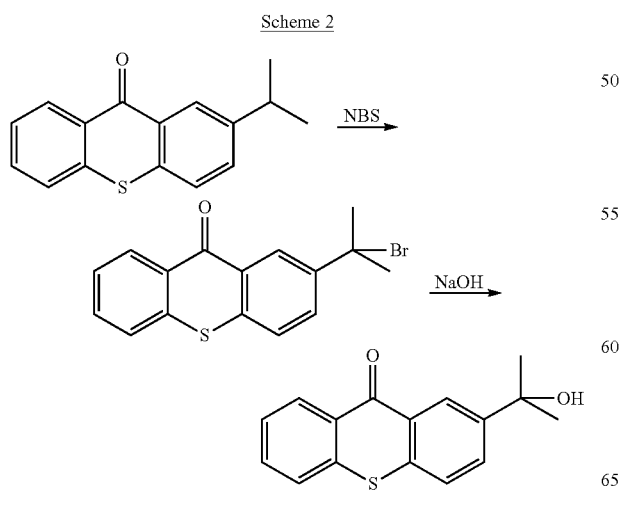

In the case of alkoxy and hydroxy substituted 9H-thioxanthen-9-one precursors, these may be made by the following synthetic routes:

Scheme 3

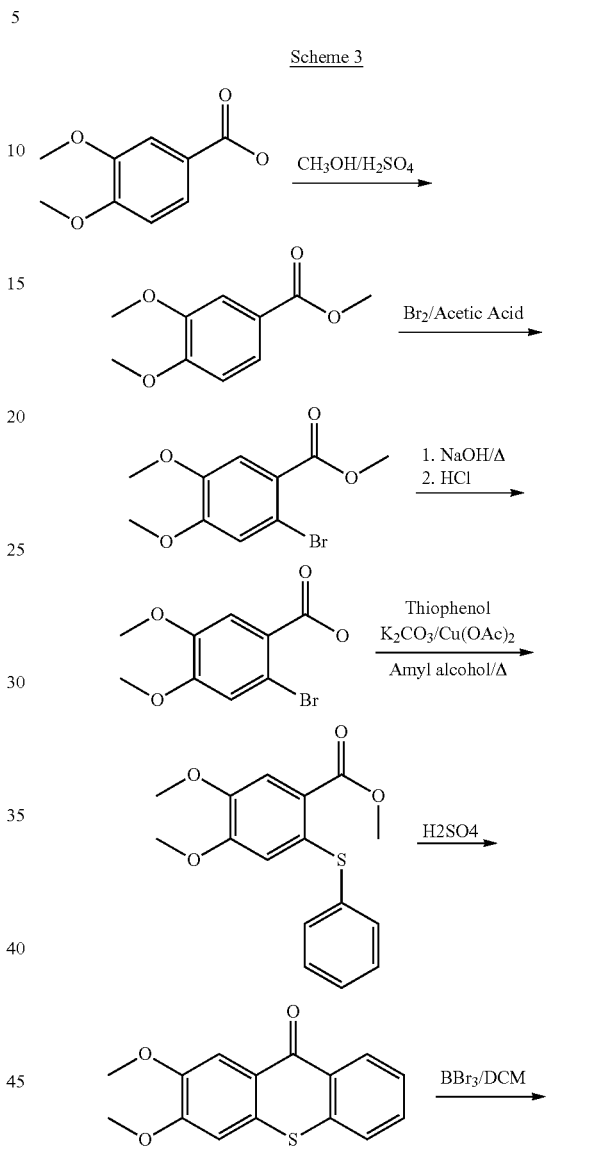

Scheme 4

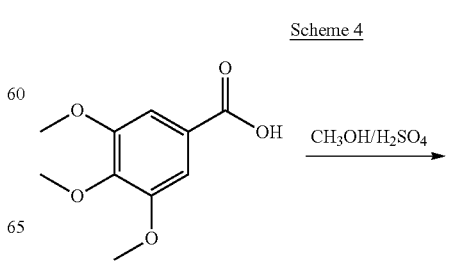

31
-continued
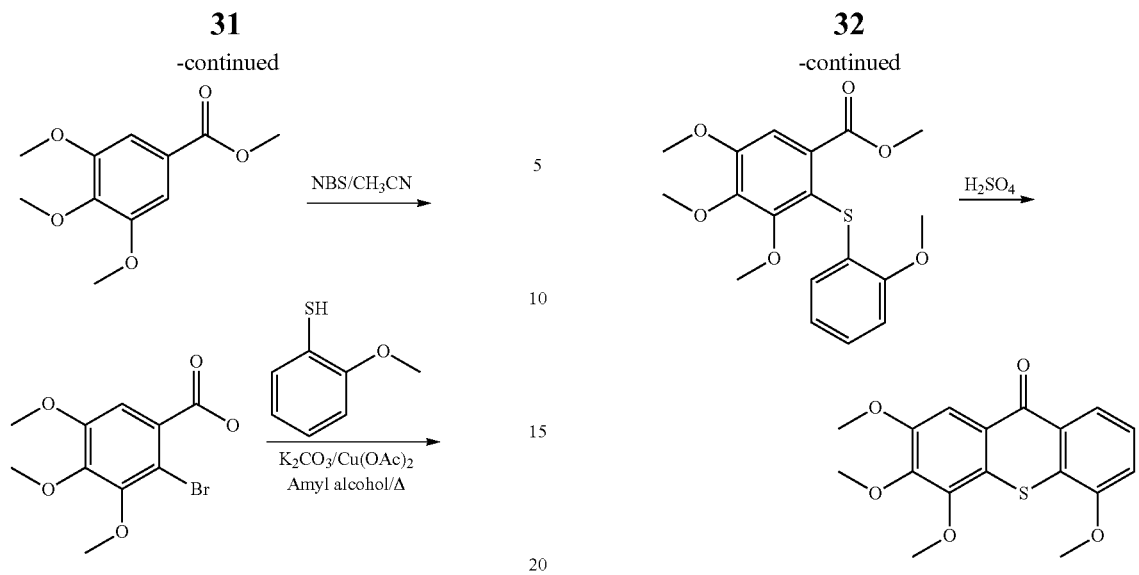
Scheme 5
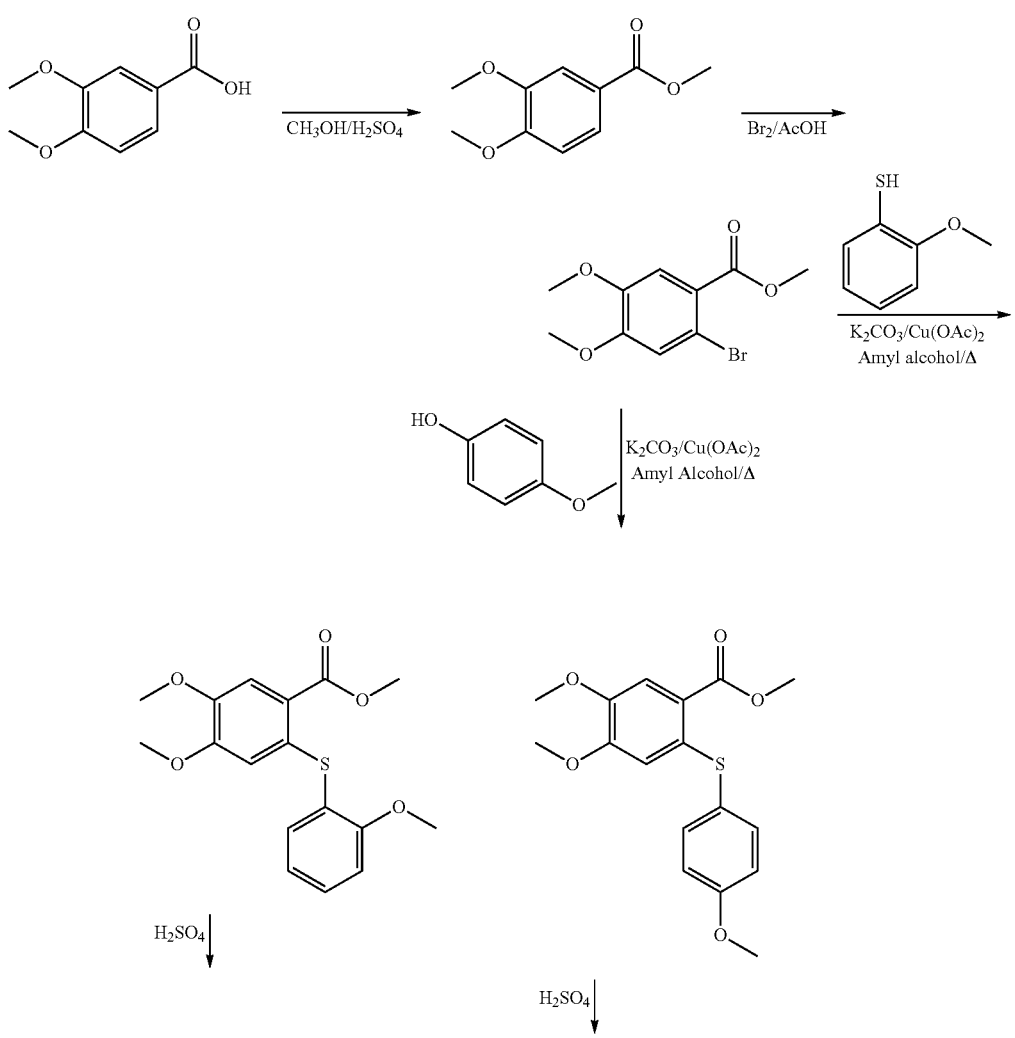

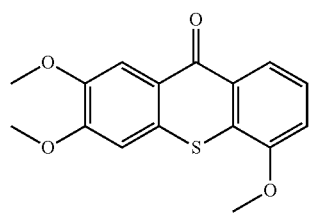
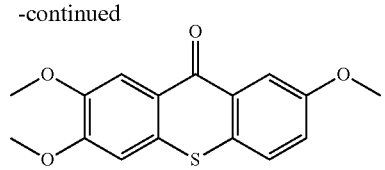

Scheme 6

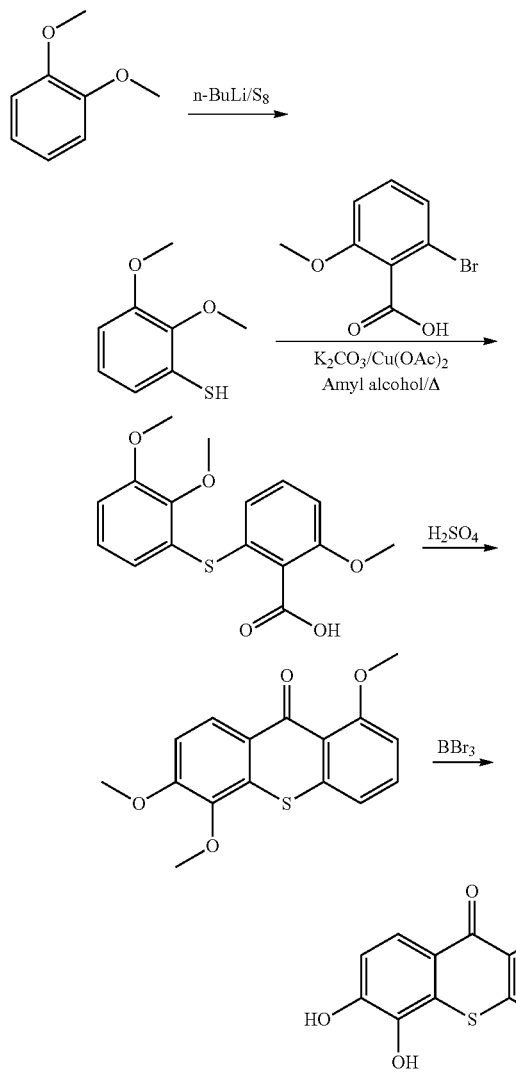

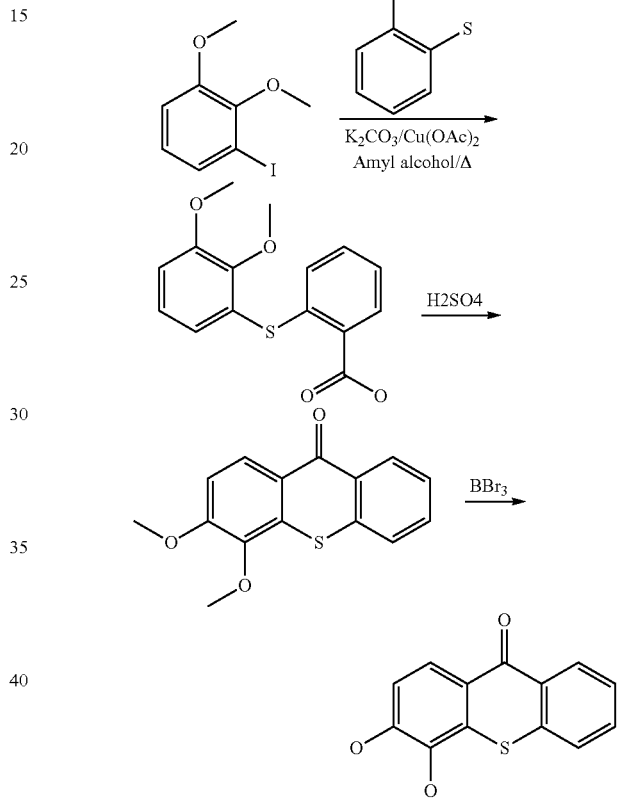

It is within the wherewithal of the person skilled in the art to modify any of the above described synthetic methods to synthesize any of the compounds within the scope of the present invention which have not explicitly been exemplified.

EXAMPLES OF THE INVENTION

The invention is illustrated by the following non-limiting examples.

Example 1

Synthesis of 3,4-Dimethoxy-9H-thioxanthen-9-one

Stage I: 2,3-dimethoxy-1-iodobenzene 1,2-Dimethoxybenzene (200 g, 1.447 mol) was dissolved in dry tetrahydrofuran (2000 ml), and under a nitrogen atmosphere was cooled to −10° C. A solution of n-butyl-lithium, 1.6M in hexane (1005 ml, 1.608 mol) was added Scheme 7

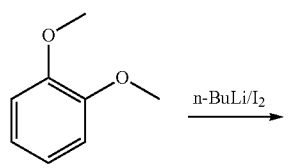

from a dropping funnel, and the reaction mixture then allowed to warm to room temperature over ~2 hours. A yellow precipitate formed as the mixture warmed up. The mixture was then cooled down to −45° C., and a solution of iodine (402 g, 1.584 mol) in dry tetrahydrofuran (2800 ml) was added fast dropwise and the reaction mixture was then allowed to warm to room temperature overnight. The reaction mixture was quenched into water containing 10% sodium metabisulphite (20 lt). The top layer was removed and the aqueous layer was extracted with diethyl ether (3×2 lt). The combined organics were washed with sodium bicarbonate solution (5 lt) and water (5 lt), and then dried over sodium sulphate. The solution was filtered through a GF/F and the solvent was removed under reduced pressure to leave an orange-brown oil, 347 g. This was adsorbed onto silica gel (600 g), and then loaded onto a wet (hexane) loaded silica gel (3000 g) column. Hexane (10 lt) was passed through then polarity was increased to 5% ethyl acetate in hexane (30 lt) to remove product. Good fractions were concentrated to an orange oil, 106 g, 0.401 mol, 27.7%, with a GC purity of 77%. This was used in the next step without further purification.

Stage II: 2-[(2,3-Dimethoxyphenyl)thio]benzoic acid 2,3-Dimethoxyiodobenzene (106 g, 0.401 mol) and Thiosalicylic acid (52 g, 0.337 mol) were dissolved in amyl alcohol (1100 ml). To this mixture was added potassium carbonate (139 g, 0.237 mol) and anhydrous copper (II) acetate (17 g, 0.0935 mol). This mixture was heated at reflux overnight (16 hours), then checked for completion by TLC (eluent 2:1 hexane/ethyl acetate).

The reaction was allowed to cool to room temperature and then poured into ~2000 ml of water, which was checked to be basic. The mixture was filtered through a GF/F fibre pad to remove suspended copper salts. The upper organic layer was separated off and discarded. The aqueous layer was extracted with diethyl ether (2×1000 ml), which were also discarded. The lower aqueous layer was acidified to pH 1 with hydrochloric acid, a brown precipitate formed. This was extracted out with ethyl acetate (3×500 ml), and dried over sodium sulphate. The solution was filtered and concentrated to a brown solid, which was triturated with t-butyl methyl ether, and collected by vacuum filtration. The solid was dried to give a pale brown powder, yield 36 g, HPLC 87.07%.

The above organic extracts were concentrated to dryness under high vacuum, and the residue was partitioned between water (1000 ml) and ethyl acetate (2×500 ml). The organic layer was dried over sodium sulphate, filtered and concentrated to a brown solid. This was triturated with t-butyl methyl ether and collected by vacuum filtration, the pale brown solid was dried to give 49 g at a purity of 99.04%, by HPLC.

Stage III: 3,4-Dimethoxy-9H-thioxanthen-9-one

2-[(2,3-Dimethoxyphenyl)thio]benzoic acid, from first crop (36 g, 0.11 mol) was added portion wise to stirred 95% sulphuric acid (360 ml), at room temperature. A slight increase in temperature was observed (19-28° C.). After 1 hour the reaction mixture was checked by TLC (2:1 hexane/ethyl acetate) and found to be complete. The reaction mixture was carefully poured into a mixture of water and ice (~2500 ml), and the resulting solids collected by vacuum filtration (very slow), and washed well with water. The solid was dissolved in ethyl acetate (3 lt) and washed with sodium bicarbonate solution, and then dried over sodium sulphate. This was filtered through a GF/F fibre pad and the resulting solution concentrated to dryness to leave an off-white solid.

Yield 23.5 g, 0.086 mol, 69.4%, with a purity of 95.24% by HPLC.

2-[(2,3-Dimethoxyphenyl)thio]benzoic acid, from second crop (49 g, 0.169 mol) was added portion wise to stirred 95% sulphuric acid (490 ml), at room temperature. A slight increase in temperature was observed (19.7-29.2° C.). After 1 hour the reaction mixture was checked by TLC (2:1 hexane/ethyl acetate) and found to be complete. The reaction mixture was carefully poured into a mixture of water and ice (~3500 ml), and the resulting solids were extracted into ethyl acetate (5 lt) and washed with sodium bicarbonate solution, and then dried over sodium sulphate. This was filtered through a GF/F fibre pad and the resulting solution concentrated to dryness to leave an off white solid.

Yield 36 g, 0.132 mol, 78.1%, with a purity of 96.45% by HPLC.

Figure 8:
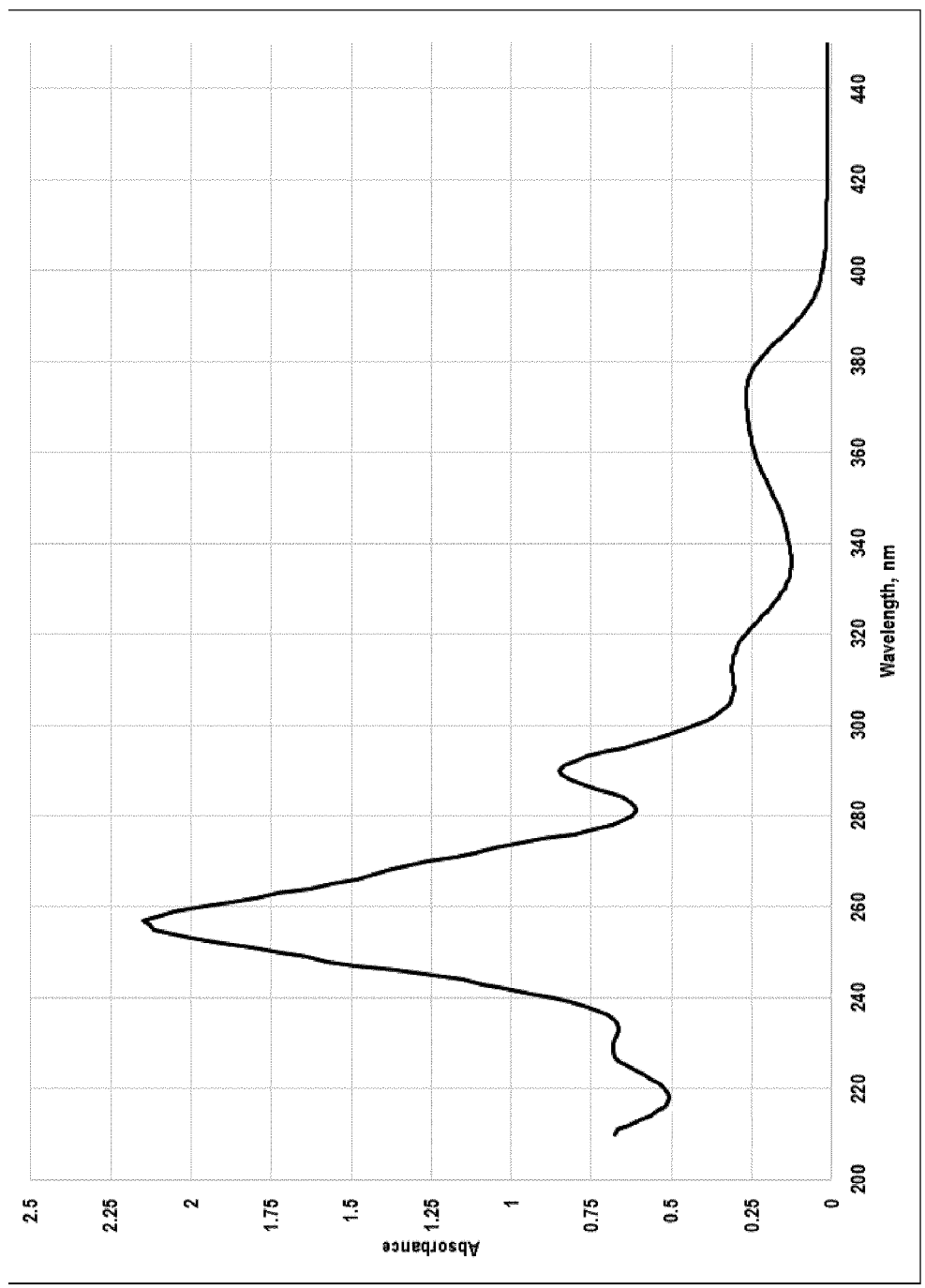
Figure 9:
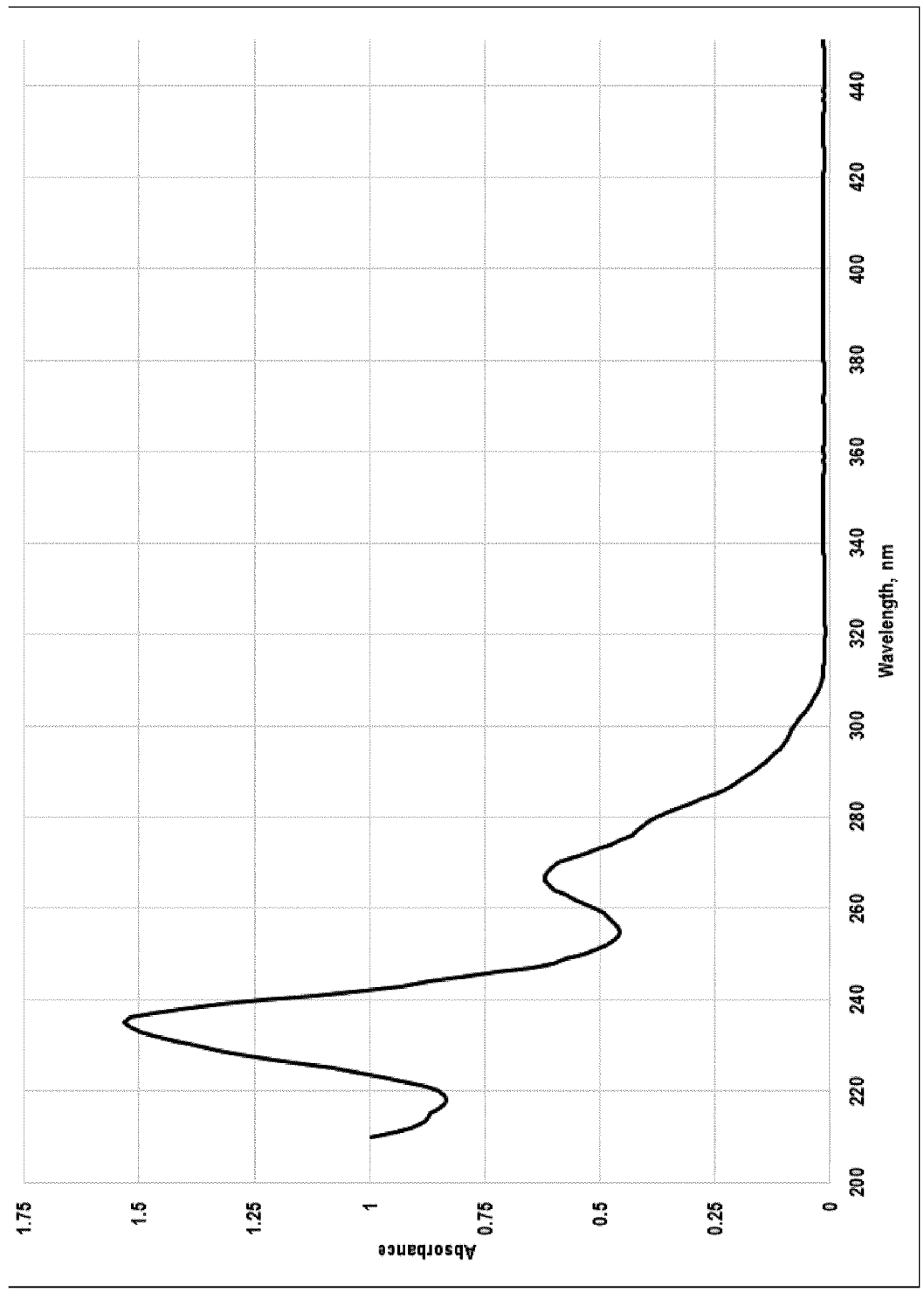
Figure 10:
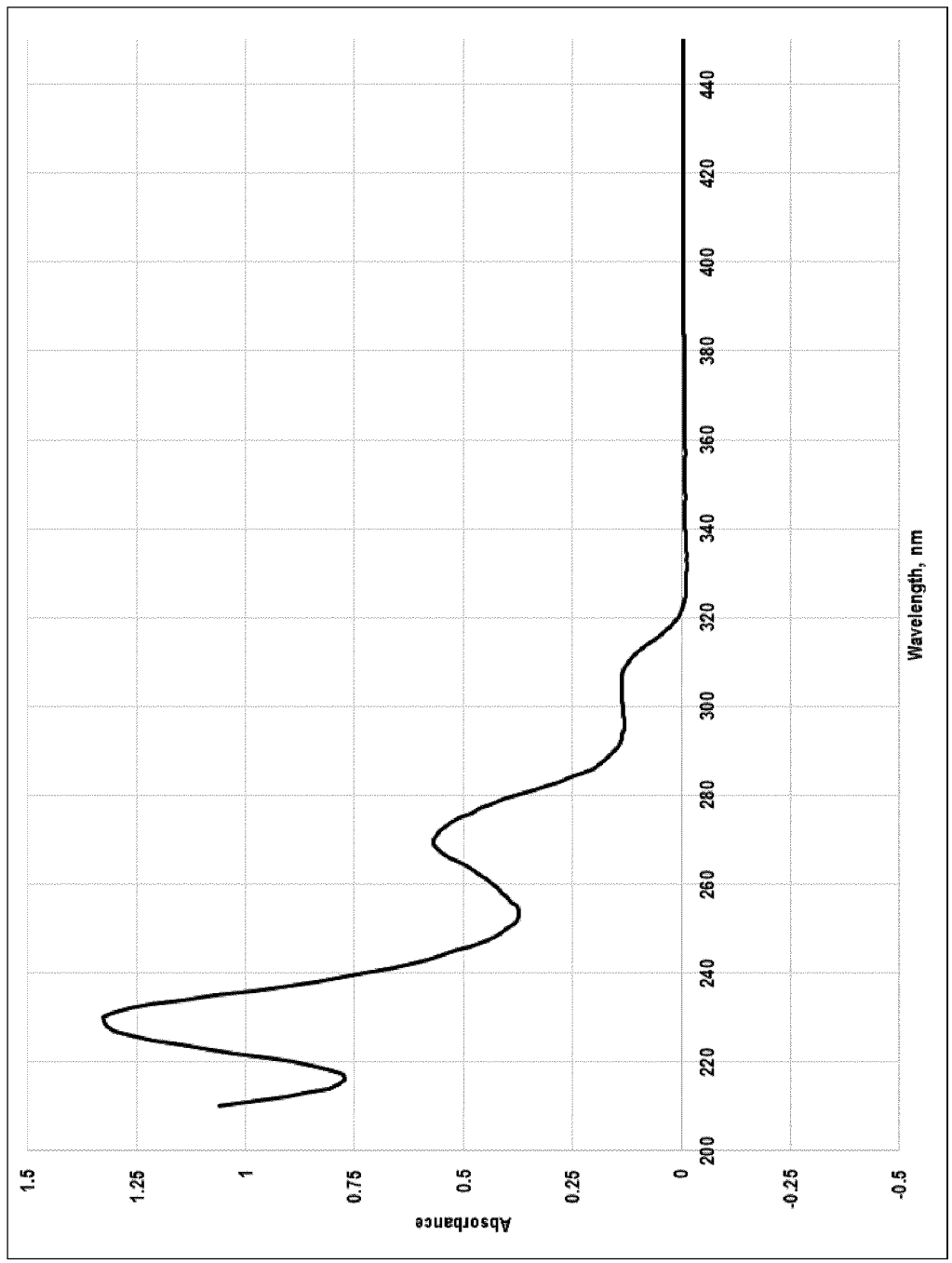
Figure 11:
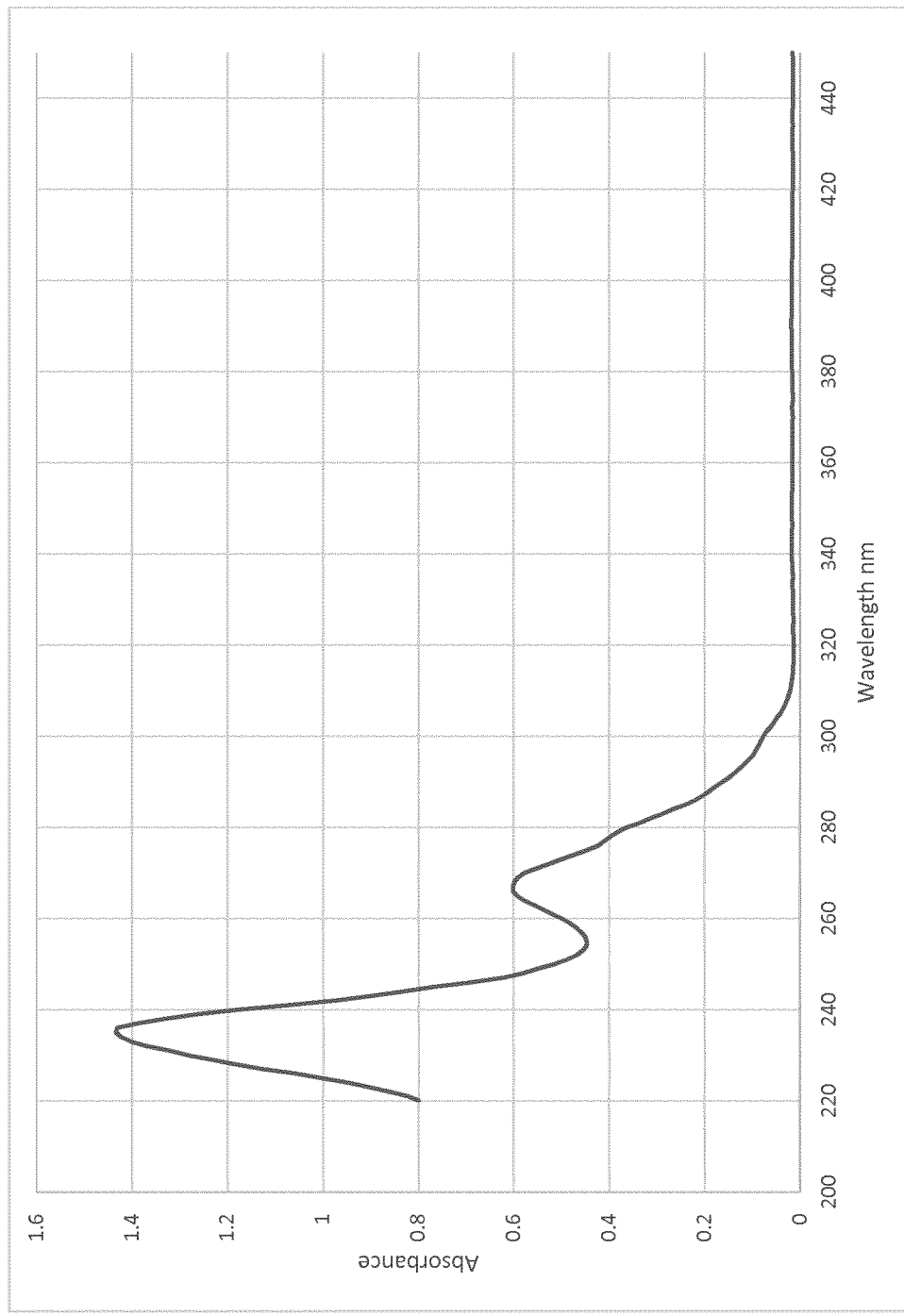
Figure 12:
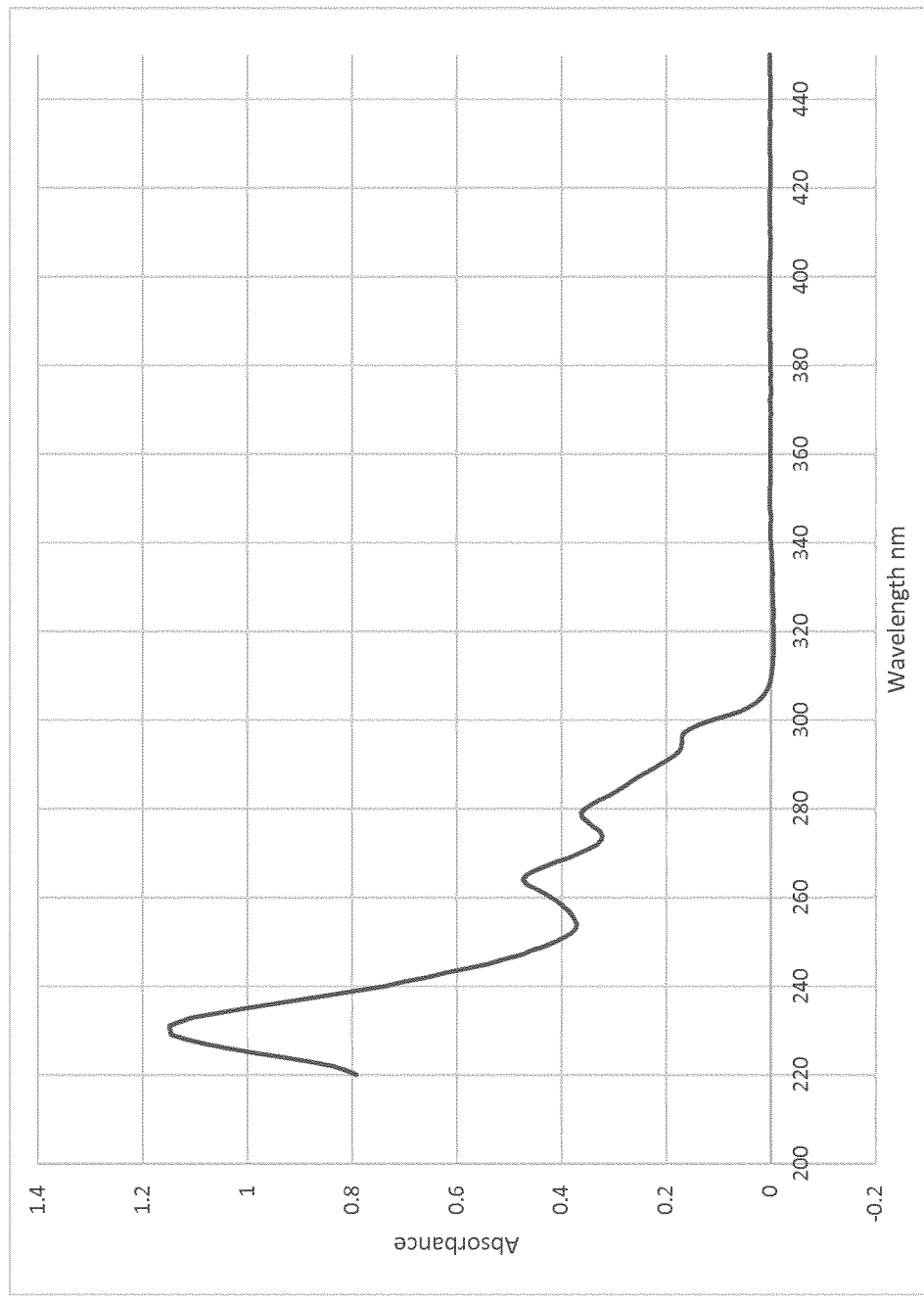
Figure 13:
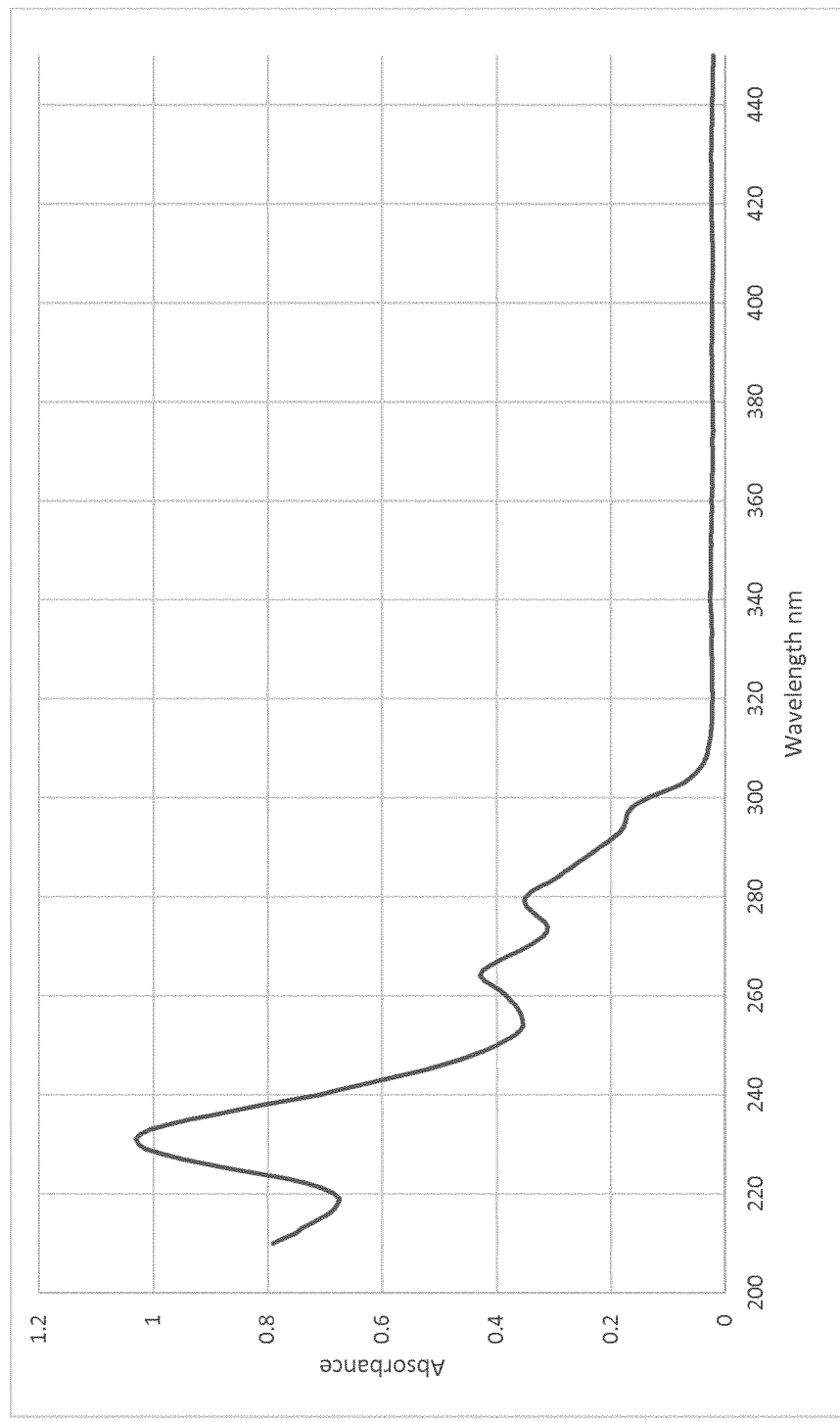
Figure 14:
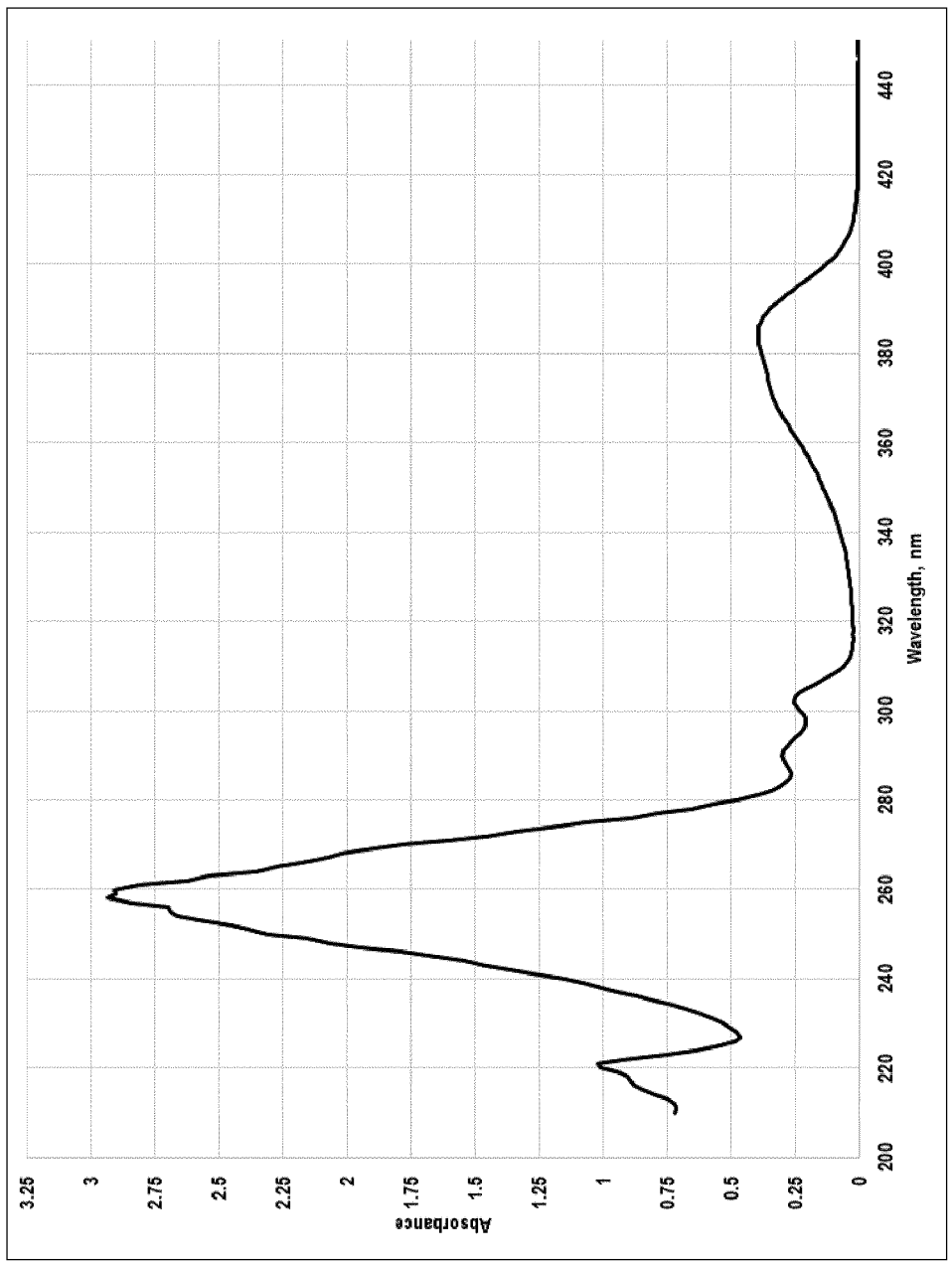
FIG. 14 shows the UV spectrum of the known photoinitiator ITX (isopropylthioxanthone)
Figure 15:
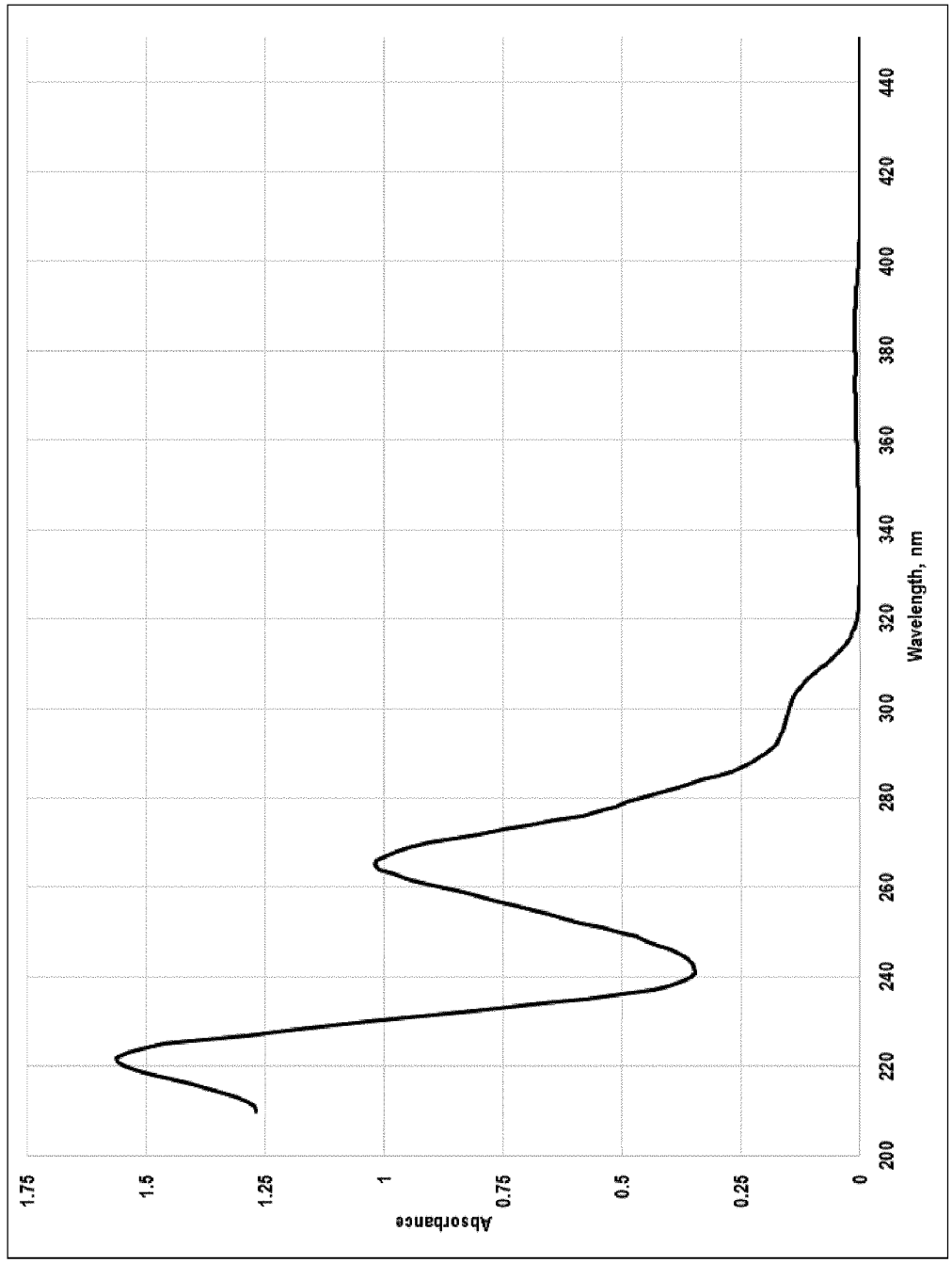
FIG. 15 shows the UV spectrum of the 1,3-dioxolane protected version of the known photoinitiator ITX.

The UV absorbance spectrum for this compound is shown in FIG. 8.

Example 2

Synthesis of 3,4-Dihydroxy-9H-thioxanthen-9-one

A solution of 3,4-dimethoxy-9H-thioxanthen-9-one (47 g, 0.173 mol.) in dichloromethane (1600 ml) was added to a solution of boron tribromide (38 ml, 98.8 g, 0.394 mol, 2.1 eq.) in dichloromethane (940 ml), under a nitrogen atmosphere at ⁻20° C. An immediate deep purple colour formed, which gradually turned to a deep red. The reaction was stirred overnight warming to room temperature. TLC (1:1 hexane/ethyl acetate) showed the reaction to be complete. The reaction was poured onto water/ice (5000 ml) and stirred for 15 minutes, a solid formed. The product was extracted out with ethyl acetate (3×3 lt), and the combined organics were washed with sodium chloride solution, dried over sodium sulphate and then filtered through a GF/F fibre pad. The solvent was removed in vacuo to leave a thick slurry, which was allowed to stand overnight. The solid was collected by filtration and washed on the filter with ethyl acetate and t-butyl methyl ether and dried to constant weight.

Yield 35 g, 82.7%, HPLC purity was 98.78%.

The filtrates were concentrated to get a second crop, which gave 1.7 g @93.03% purity.

Figure 7:
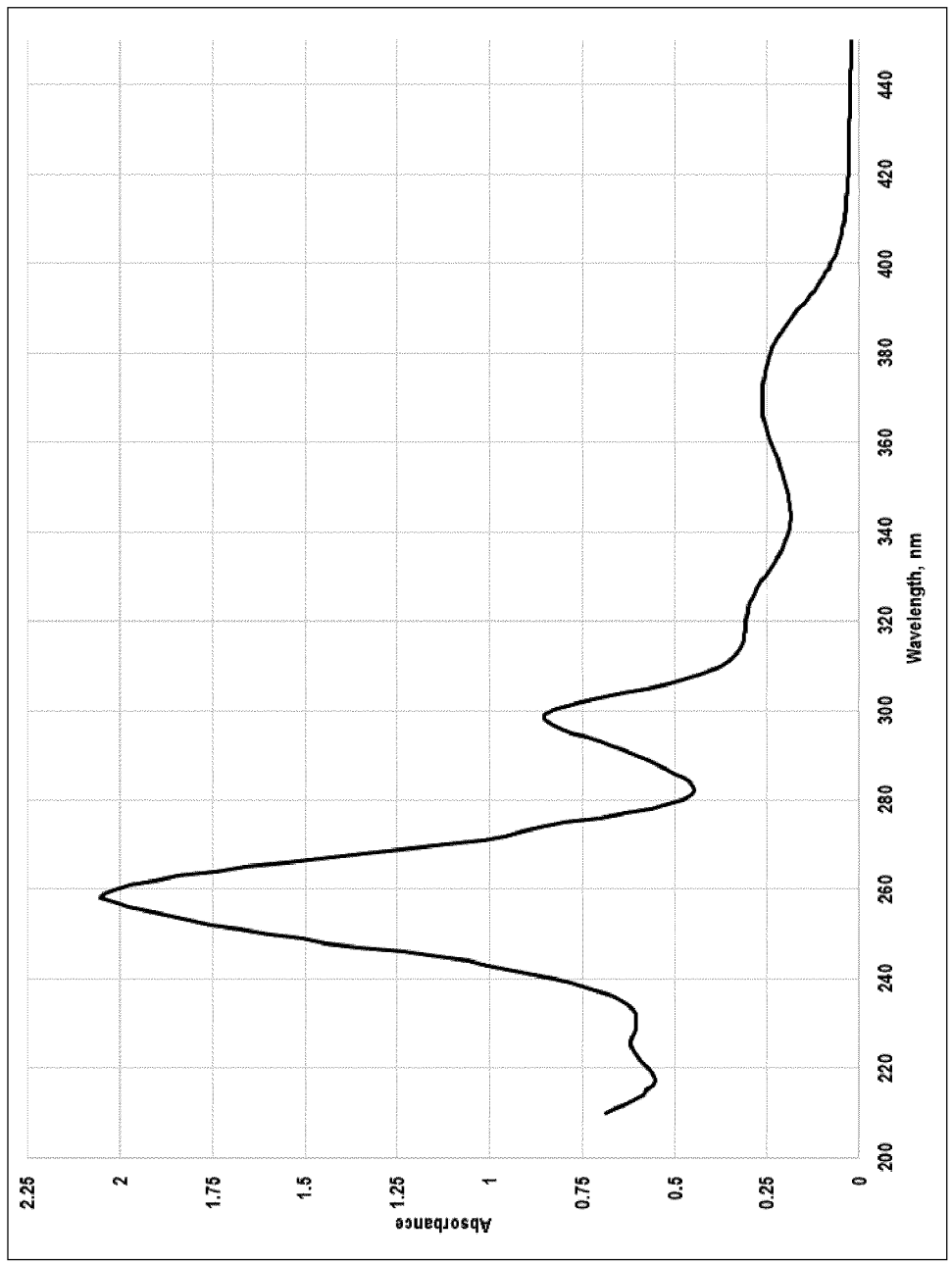

The UV absorbance spectrum for this compound is shown in FIG. 7.

Example 3

Synthesis of 1,5,6-Trimethoxy-9H-thioxanthen-9-one

Stage I: 2,3-Dimethoxybenzenethiol 1,2-Dimethoxybenzene (710 g, 5.139 mol) and N,N,N,N-tetramethylethylenediamine (8 ml, 53.5 mmol) were dissolved in dry tetrahydrofuran (7100 ml), under a nitrogen atmosphere. The mixture was cooled to ⁻45° C., and n-butyllithium solution 1.6M in hexane (3550 ml, 5.68 mol) was added via a dropping funnel. The reaction was allowed to stir and warm to room temperature over 2 hours, (72.3% unlithiated material left), a yellow precipitate gradually formed. After 21 hours the mixture showed 45.4% lithiated product, the reaction was cooled to −70° C., and elemental sulphur (95 g, 2.96 mol) was added portion wise below −60° C., an immediate exotherm was observed and a brown solution formed. The reaction was left to stir and warm to room temperature overnight.

The reaction mixture was poured into ~20 lt of water, and the upper organic layer discarded. The aqueous solution was extracted with diethyl ether (3×3000 ml) and this was discarded. The aqueous layer was acidified to pH 1 with hydrochloric acid, and extracted with diethyl ether (3×3000 ml). The combined organic extracts were washed with water (2000 ml) and then dried over sodium sulphate. This was filtered through a GF/F and the solvent removed to leave a brown oil, 531 g @84.3%=448 g, 51.2% yield (material still contained 11.2% 1,2-dimethoxybenzene.

Stage II: 2-[(2,3-Dimethoxyphenyl)thio]-6-methoxybenzoic acid 2,3-Dimethoxybenzenethiol (105 g @84.3%, 0.52 mol) and 2-bromo-6-methoxybenzoic acid (89 g, 0.385 mol) were dissolved in amyl alcohol (1500 ml), and stirred under a nitrogen atmosphere. To this was added anhydrous potassium carbonate (172.5 g, 1.248 mol) and anhydrous copper (II) acetate (21 g, 0.1156 mol). The reaction was heated to reflux overnight (19 hours), and then checked for completion by TLC (eluent 2:1 hexane/ethyl acetate). The reaction was cooled to room temperature and the amyl alcohol removed under high vacuum, the residue was dissolved in water (5 lt). The aqueous was extracted with diethyl ether (3×1 lt) and discarded. The aqueous layer was then acidified to pH 1 with c.hydrochloric acid. The product was extracted with dichloromethane (3×500 ml), and the combined organics were dried over sodium sulphate, and filtered through a GF/F. The solvent was removed in vacuo to leave a thick brown oil, which crystallised overnight. The solid was triturated with t-butyl methyl ether, and collected by filtration, and dried to leave 32 g @98.36% by HPLC.

The filtrates were concentrated to a brown oil, 52 g @80.56% purity by HPLC, which was used in the next step without further purification.

Stage III: 1,5,6-Trimethoxy-9H-thioxanthen-9-one

Sulphuric acid (500 ml) was carefully added to the crude 2-[(2,3-dimethoxyphenyl)thio]-6-methoxybenzoic acid (52 g) and the mixture stirred at room temperature for~2 hours. TLC (eluent 1:1 ethyl acetate/hexane) indicated that the reaction was complete. The reaction mixture was poured into ice/water (5 lt), and the product extracted out with dichloromethane (3×1 lt), and the combined organic extracts were washed with saturated sodium bicarbonate solution (1 lt). The organic layer was dried over sodium sulphate, filtered through a GF/F and concentrated to dryness. The residue was triturated with ethanol and the pale brown solid collected by filtration. The product was dried to give 12.2 g, which was combined with the next reaction product. [0148] 2-[(2,3-Dimethoxyphenyl)thio]-6-methoxybenzoic acid (32 g, 0.0999 mol) was added portion wise to stirring sulphuric acid (320 ml) at room temperature.

The mixture was stirred for 1 hour then quenched into ice/water (~3.2 lt) and left to stand overnight. Work up was as above, and the resulting solid combined with that from the above reaction.

Total yield 18 g, with a HPLC purity of 96.65%.

Figure 6:
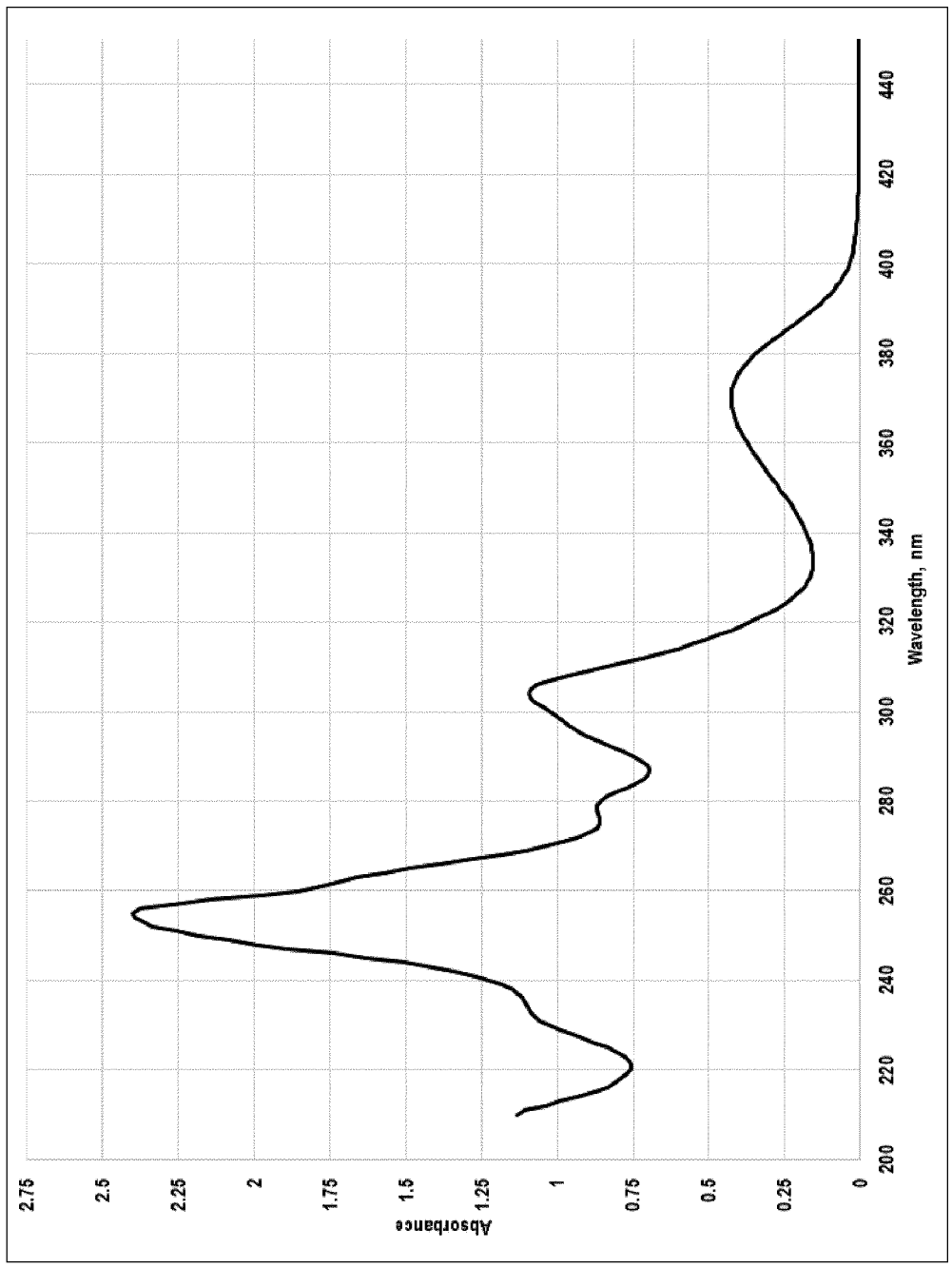

The UV absorbance spectrum for this compound is shown in FIG. 6.

Example 4

Synthesis of 1,5,6-trihydroxy-9H-thioxanthen-9-one

The 1,5,6-trihydroxy compound was made by demethylating the 1,5,6-trimethoxy compound from Example 3 using boron tribromide.

Boron tribromide (12.85 g, 5 ml, 0.0513 mol.) was dissolved in dichloromethane (100 ml), and under a nitrogen atmosphere was cooled to −20° C.

A solution of 1,5,6-trimethoxy-9H-thioxanthen-9-one (5 g, 0.0165 mol) in dichloromethane (170 ml) was added drop wise. The reaction was allowed to stir and warm to room temperature overnight (note an immediate deep orange colour was observed). TLC (eluent toluene/ethyl acetate/formic acid, 5:4:1) showed the reaction to be complete. The reaction mixture was poured into a mixture of ice and water. A red precipitate formed, which was filtered through GF/F paper. The aqueous layer was extracted with ethyl acetate (2×100 ml), dried over sodium sulphate, filtered and concentrated to a red solid (<1 g). The red solid was re-extracted with ethyl acetate several times, and the solution filtered through a pad of silica gel to remove some baseline material. The solution was concentrated to an orange/red solid, total yield 1.9 g, HPLC 79.81% (still shows some starting material. $^1$H NMR indicates that the desired material was present.

Example 5

Synthesis of 2,3-dimethoxy-9H-thioxanthen-9-one

Stage I: Methyl 3,4-dimethoxybenzoate 3,4-dimethoxybenzoic acid (1000 g, 5.49 mol) was suspended in methanol (5 lt), and stirred. To this was added 95% sulphuric acid (200 ml), and the mixture was then heated at reflux for ~15 hours, before cooling to room temperature overnight. The reaction mixture was carefully poured into saturated sodium bicarbonate solution with stirring, a white foamy precipitate formed. The product was extracted out with t-butyl methyl ether (3×4 lt), then dried over sodium sulphate. The sodium sulphate was removed by filtration through a GF/F and the solvent removed under reduced pressure, to give a white solid, 1070 g, GC 99.7%.

Stage II: Methyl 2-bromo-4,5-dimethoxybenzoate

Methyl 3,4-dimethoxybenzoate (1070 g, 5.45 mol) was dissolved in glacial acetic acid (5 lt), and cooled to 10° C. (any colder and it sets solid). A solution of bromine (880 g, 5.51 mol) in acetic acid (2.5 lt) was added over ~4 hours keeping the temperature ~10° C. After stirring overnight the reaction was ~50% brominated, this did not change over a further 3 days stirring, and addition of a catalytic amount of iron powder. The reaction was carefully poured into water (25 lt) containing ~10% sodium metabisulphite, a white solid formed. The solid was collected by filtration and washed well on the filter with DI water (5 lt), the solid was dried overnight in a fan oven at 50° C.

Yield 1013 g @82.1% purity by GC.

The product was purified by dissolving in refluxing methanol (2 lt), then allowing to cool slowly to room temperature, leaving to stand for 3 days. The crystalline solid was collected by filtration and washed on the filter with a small amount of methanol, and drying to constant weight. This gave a yield of 468 g (~31%) with a GC purity of 99.0%.

A second crop (52 g) was obtained with low purity (86%), which was discarded.

Stage III: 2-Bromo-4,5-dimethoxybenzoic acid

Methyl 2-bromo-4,5-dimethoxybenzoate (367 g, 1.334 mol) was added to a solution of potassium hydroxide (112 g, 2.00 mol) in demineralised water (2 lt).

The suspension was heated to reflux for 2 hours, by which time a clear solution resulted. A TLC (eluent 1:1 ethyl acetate/hexane) indicated the reaction was complete. The solution was cooled to room temperature, and diluted with demineralised water (5 lt), then acidified to pH 1 with c.hydrochloric acid. The resulting white solid was collected by filtration, and washed well on the filter with demineralised water (~5 lt), the solid was pulled dry for several hours, before drying to constant weight in a fan oven at 50° C.

Yield, 339 g, 1.30 mol, 97.45%, purity by HPLC was 99.64%.

Stage IV: 4,5-dimethoxy-2-(phenylthio)benzoic acid

2-Bromo-4,5-dimethoxybenzoic acid (121 g, 0.463 mol) was dissolved in amyl alcohol (1500 ml), under a nitrogen atmosphere. To this was added, thiophenol (56 g, 0.508 mol), potassium carbonate (207 g, 1.5 mol) and anhydrous copper (II) acetate. The mixture was stirred and heated at reflux overnight. The reaction was then cooled to ~35° C. and the solvent removed under high vacuum, the resulting residue was partitioned between water (3 lt) and ethyl acetate (3 lt). The two layers were separated and the aqueous layer was extracted with ethyl acetate (2×500 ml), and discarded. The aqueous layer was acidified to pH 1 with hydrochloric acid (32%). The product was extracted out with ethyl acetate (3×1000 ml), and the combined extractions were dried over sodium sulphate, then filtered through a GF/F. The solvent was removed to leave an off white solid (106 g) which triturated with t-butyl methyl ether, then left to stand overnight. The solid was collected by filtration, washed with t-butyl methyl ether, and dried to constant weight. This gave an off white solid, 85 g, Purity by HPLC 84.22%. (7 g of second crop material @95.66% was obtained).

This was trialed in the next step and was found to give good material without needing purification.

Some material was obtained from the ester (methyl 2-bromo-4,5-dimethoxybenzoate) but required extra work to get pure enough before it could be cyclised.

Stage V: 2,3-Dimethoxy-9H-thioxanthen-9-one 4,5-Dimethoxy-2-(phenylthio)benzoic acid (112 g @84.22%, 0.349 mol) was added portion wise to stirred 95% sulphuric acid (1200 ml), a rise in temperature from 18.9-28.6° C. was noted. The mixture was stirred at room temperature overnight. The reaction was shown to be complete by TLC (eluent ethyl acetate/hexane 1:1). The reaction mixture was poured into ice/water (8 lt), and the solid extracted out with ethyl acetate (3×5 lt). The ethyl acetate solution was washed with saturated sodium bicarbonate solution (5 lt), and dried over anhydrous sodium sulphate. The salts were removed by filtration through a GF/F pad and the solvent removed under reduced pressure to leave a pale yellow solid. This was triturated with a small volume (~150 ml) of ethanol and the solid collected by vacuum filtration.

This gave the product (81 g, 85.1%) as a pale yellow powder, purity by HPLC was 99.32%, and 100% by GLC.

The UV absorbance spectrum for this compound is shown in FIG. 1.

Example 6

Synthesis of 2,3-Dihydroxy-9H-thioxanthen-9-one

Boron tribromide (9.7 g, 0.0387 mol) was dissolved in dichloromethane (100 ml), under a nitrogen atmosphere. This solution was cooled to ⁻20° C., and then a solution of 2,3-dimethoxy-9H-thioxanthen-9-one (5 g, 0.0184 mol) (from Example 3) in dichloromethane (100 ml) was added dropwise at ⁻20° C. A deep yellow solution formed which gradually darkened to orange. The reaction was allowed to warm slowly to room temperature, and stirred for 4 days. TLC indicated that the reaction was complete (hexane/ethyl acetate 2:1), so was quenched by the drop wise addition of water (250 ml), and was then stirred for 1 hour to ensure hydrolysis of the boron complex. On addition of ethyl acetate (500 ml) an emulsion formed. This was filtered through a GF/F to try to break it up. The organic layer was separated and washed with saturated sodium bicarbonate solution, then dried over sodium sulphate, and filtered through GF/F. The clear solution was concentrated to leave a yellow solid (first crop). The solid filtered off above was dissolved in tetrahydrofuran and found to be also product (by TLC). This solution was filtered through a GF/F and dried, and combined with the first crop material, and triturated with t-butyl methyl ether. This was collected by filtration and dried to give the product as a yellow powder, 3.9 g, 86.8%. The purity by HPLC was 92.59%, and the structure was confirmed by $^1$H NMR.

Figure 2:
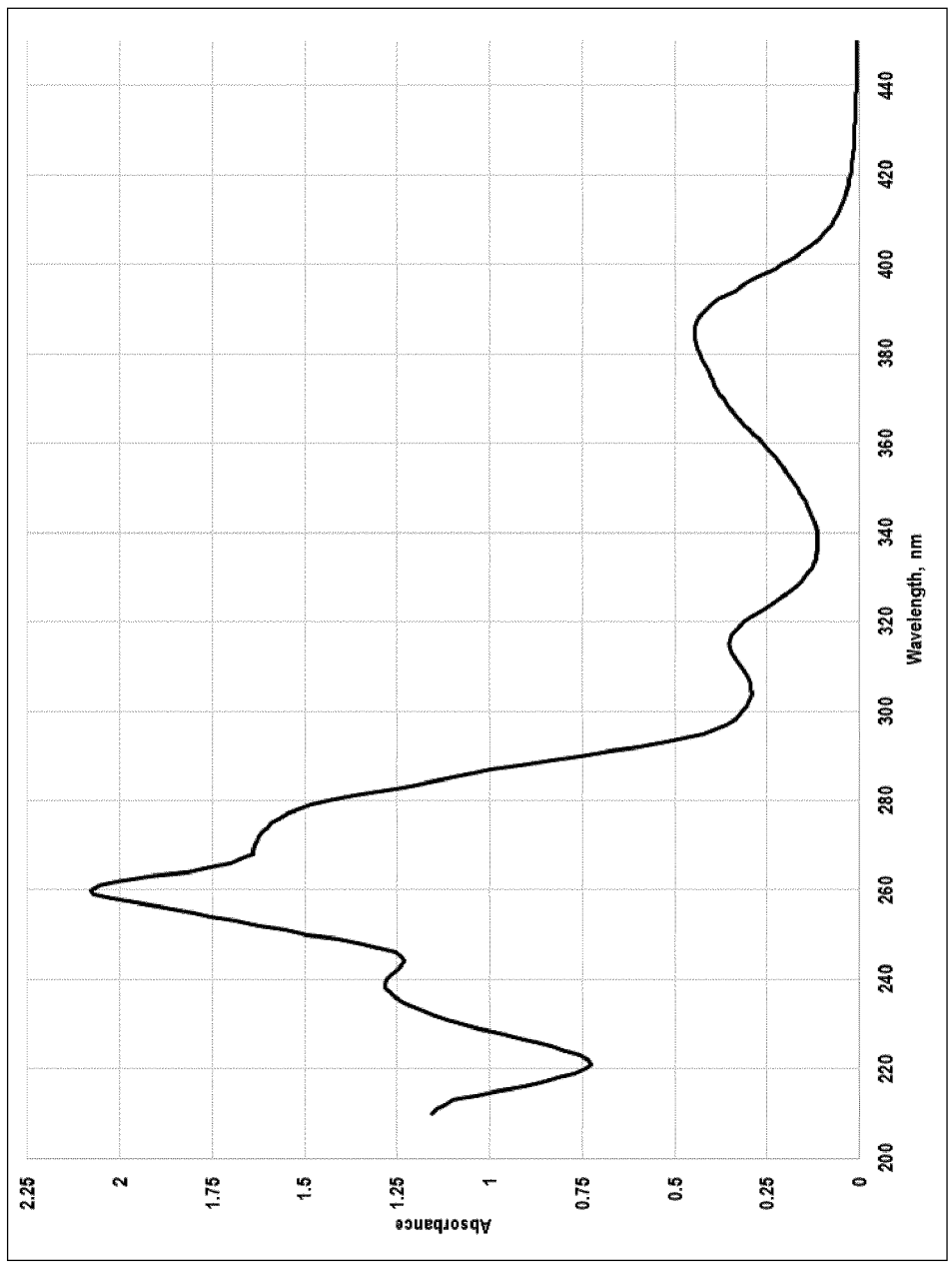

The UV absorbance spectrum for this compound is shown in FIG. 2.

Example 7

Synthesis of 2',3'-Dimethoxyspiro[(1.3)-dioxolane-2,9'-thioxanthene]

Stage I: 2,3-Dimethoxy-9H-thioxanthen-9-thione

Trial 1

2,3-Dimethoxy-9H-thioxanthen-9-one (5 g, 0.0184 mol) was added to toluene (150 ml) under a nitrogen atmosphere. To this was added Lawessons reagent (2,4-Bis(4-methoxyphenyl)-1,3,2,4-dithiadiphosphetane-2,4-dithione) (5.5 g, 0.0136 mol). The mixture was stirred and heated at 80° C. for 2 hours, after which a TLC (eluent 2:1 hexane/ethyl acetate) revealed that the reaction was complete. The reaction was cooled to room temperature, and diluted with hexane/dichloromethane, 4:1 (250 ml). This was then filtered through a pad of silica gel, and washed through with hexane/dichloromethane (2×250 ml). The filtrate was stripped to a brown solid, 7.8 g, GC 77.8%. Silica allows dark impurities through. The brown solid was dissolved in ethyl acetate/hexane (2:1), and filtered through a pad of silica gel, this removed baseline material but was still very dark in colour. The solvent was removed to leave a black solid. This was again dissolved in ethyl acetate/hexane (2:1) and this time passed through a pad of neutral alumina, and washed off the column with ethyl acetate/hexane (2:1). The filtrate was a bright yellow colour, this was concentrated to a red solid, 4.9 g, GC 95.7%.

Trial 2

2,3-Dimethoxy-9H-thioxanthen-9-one (5 g, 0.0184 mol) was dissolved in toluene (625 ml), under a nitrogen atmosphere. To this was added phosphorous pentasulphide (32.8 g, 0.0738 mol). The mixture was then heated at reflux overnight, a TLC (eluent hexane/ethyl acetate 2:1) showed the reaction to be complete. The reaction was cooled to room temperature and filtered through a GF/F fibre pad. The filter cake was washed with dichloromethane, and the combined organic filtrates were concentrated to a dark solid, this was dissolved in dichloromethane/hexane (1:1) and filtered through a pad of acidic alumina. The filtrate was stripped to a dark solid, 4 g. This was used in next step as is.

Stage II: 2',3'-Dimethoxyspiro[(1.3)-dioxolane-2,9'-thioxanthene]

2,3-Dimethoxy-9-H-thioxanthen-9-thione (4 g, 0.0139 mol) was suspended in acetonitrile (85 ml), under a nitrogen atmosphere. To this was added ethylene glycol (1.2 g, 0.0193 mol), triethylamine (7.5 ml), and then silver trifluoroacetate (11.6 g, 0.0525 mol) was finally added. The mixture was stirred at room temperature (a slight 8° exotherm was noted), and followed by TLC (eluent hexane/ethyl acetate 2:1). The reaction was complete after stirring overnight. A GC indicated no starting material, and 84.4% product. The acetonitrile and trimethylamine were removed in vacuo, and the residue was partitioned between ethyl acetate (100 ml) and brine (100 ml). This was filtered through a GF/F, and the filter cake was washed with ethyl acetate (100 ml). The two layers were separated and the aqueous layer was extracted with further ethyl acetate (2×100 ml). The combined organics were dried over sodium sulphate, and then filtered through a GF/F fibre pad. The filtrate was concentrated to an orange oil, 6 g which was triturated with t-butyl methyl ether, the solid was collected and dried to give 5.6 g.

Purification was carried out on this material.

The crude material was dissolved in isopropyl alcohol (50 ml) under a nitrogen atmosphere, and warmed to 50-55° C. To this was added sodium borohydride (0.5 g, 0.0132 mol), an immediate colour change (orange to yellow) occurred, after 6 hours, ketone was still present, so a further 1 g of sodium borohydride was added and heating continued for a further 8 hours. The reaction was allowed to stir and cool overnight. A GC showed mainly a single peak, the reaction was poured into water and extracted out with ethyl acetate (2×100 ml) and dried over sodium sulphate, filtered through a GF/F and concentrated to a sticky oil. This was dissolved in toluene (200 ml) and passed through a small pad of basic alumina, and washed through with more toluene. The filtrate was concentrated to a gummy solid which slowly crystallises overnight, GC 96%. The solid was triturated with a few ml of ethanol and cooled in the fridge for 1-2 hours. The solid was collected by filtration and washed with t-butyl methyl ether. This dried to give 2.5 g of a white solid. This material and the 0.52 g from above were dissolved in dichloromethane, then concentrated to dryness, the residue was triturated with t-butyl methyl ether (~20 ml) and the white solid was collected by filtration, and washed on the filter with a few ml of t-butyl methyl ether.

The purity by HPLC was 99.9% and the structure was confirmed by $^1$H NMR.

The UV absorbance spectrum for this compound is shown in FIG. 2.

Example 8

Synthesis of 2,3,5-Trimethoxy-9H-thioxanthen-9-one

Stage I: 4,5-Dimethoxy-2-[(2-methoxyphenyl)thio] benzoic acid

2-Bromo-4,5-dimethoxybenzoic acid (85 g, 0.326 mol) and 2-methoxybenzenethiol (50 g, 0.359 mol) were dissolved in amyl alcohol (1275 ml), under a nitrogen atmosphere. To this solution was added anhydrous potassium carbonate (146.3 g, 1.06 mol), and anhydrous copper (II) acetate (10 g). The mixture was then heated at reflux for 48 hours, by which time a TLC (ethyl acetate×2) showed the reaction to be virtually complete. The solvent was removed under high vacuum, and the residue was dissolved in water (2 lt). The aqueous phase was extracted with ethyl acetate (2×1 lt) and set aside. The aqueous phase was acidified to pH 1 with 32% hydrochloric acid, and the resulting solid was collected by filtration, and then successively washed on the filter with water, ethanol ethyl acetate and t-butyl methyl ether. The pale yellow solid was dried to constant weight, to give 67 g, 0.209 mol, 64.1% with a HPLC purity of 93.15%. The structure was confirmed by Proton NMR.

Stage Ia: 4,5-Dimethoxy-2-[(2-methoxyphenyl)thio] benzoyl chloride 4,5-Dimethoxy-2-[(2-methoxyphenyl)thio]benzoic acid (10 g, 0.313 mol) was suspended in dichloromethane (50 ml), and stirred under a nitrogen atmosphere. To this was added oxalyl chloride (8 ml, 0.0932 mol) and 5 drops of N,N-dimethylformamide. The reaction was stirred at room temperature for 1 hour, the solid changing colour from yellow to orange. The mixture was then heated at reflux for 4 hours, the solid dissolves and a clear orange red solution results. The solvent and volatiles were removed under vacuum, and more dichloromethane was added, and evaporated off to leave a thick orange/brown oil, which slowly solidifies. The yield was 11 g, and was stored under nitrogen before being used in the next stage without further purification.

Stage II: 2,3,5-Trimethoxy-9H-thioxanthen-9-one 4,5-Dimethoxy-2-[(2-methoxyphenyl)thio]benzoyl chloride (11 g, 0.0325 mol) was dissolved in dichloromethane (135 ml), and cooled to 0-⁻5° C. under a nitrogen atmosphere. Aluminium chloride (6.3 g, 0.0472 mol) was added in small portions, the solution turned red and solid precipitated out. The mixture was stirred for 30 minutes at room temperature, and then cooled back to 0° C. The reaction was quenched by the addition of 2M hydrochloric acid (150 ml), and the allowed to warm and stir at room temperature for 30 minutes. The solid present was collected by filtration, and the aqueous was extracted with dichloromethane (2×300 ml). The combined organics were washed with 10% potassium hydroxide solution (2×100 ml), and then dried over sodium sulphate. The inorganics were filtered out through GF/F, and solvent removed to leave a yellow solid, 6 g. After further extraction of the aqueous only, 0.5 g of product was collected. The two solids were triturated with methanol (50 ml), and then collected by filtration, and dried.

Yield 5.7 g, purity by HPLC 84.31%.

The solid which was filtered earlier was dried to give 2.24 g, HPLC 95.62%, containing inorganics.

Both samples were recrystallized from toluene (85-95 volumes), with a hot filtration through a GF/F fibre pad to remove insoluble material.

5.7 g gave 3.5 g @91.39%.

Figure 3:
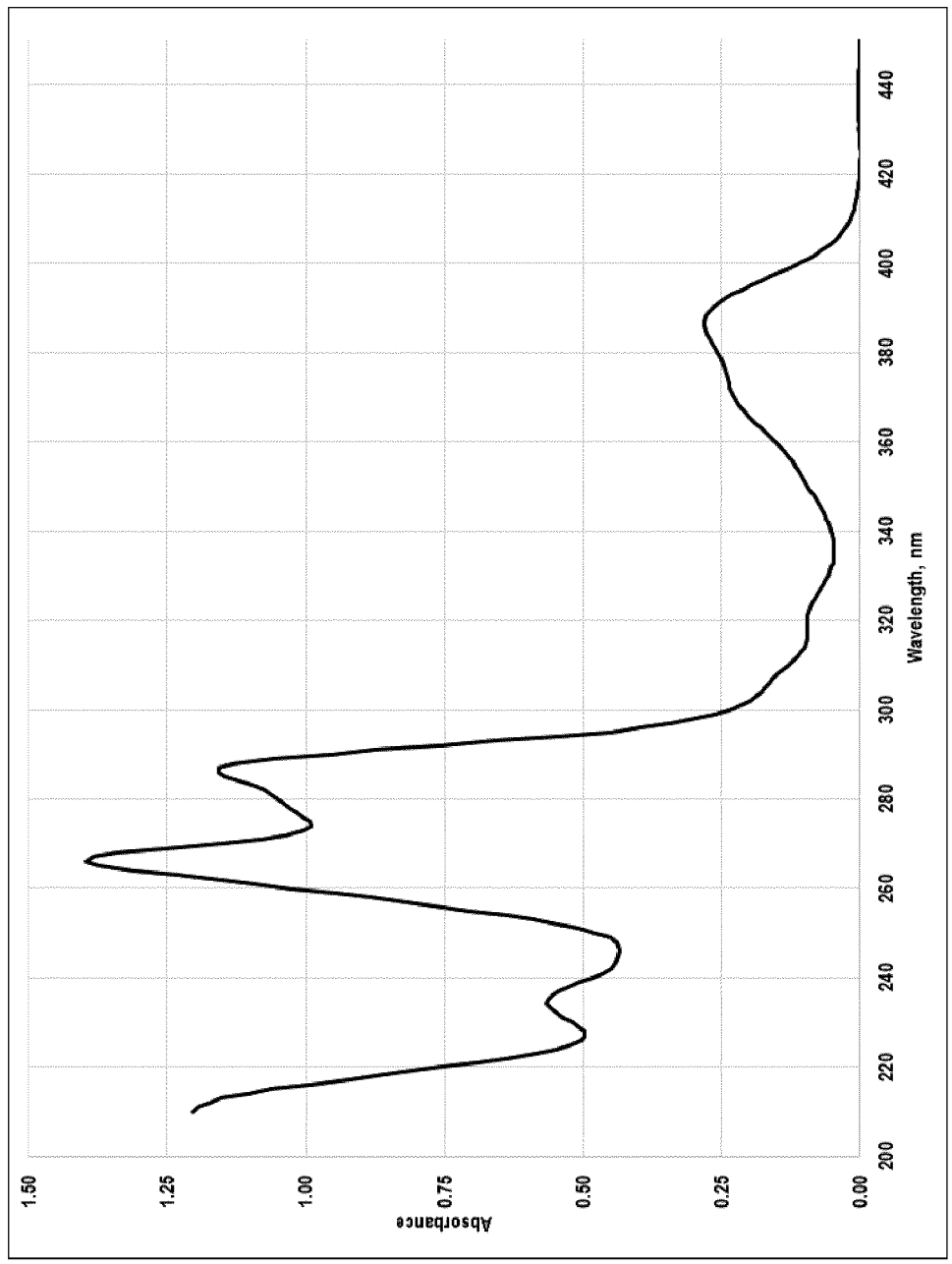

The UV absorbance spectrum for this compound is shown in FIG. 3.

The carbonyl compound of this example may be reacted with ethylene glycol per Scheme 1 above to obtain the compound 2,3,5-trimethoxy spiro[(1,3)dioxolane-2,9'-thioxanthene].

Example 9

Synthesis of 2,3,7-Trimethoxy-9H-thioxanthen-9-one

Stage I: 4,5-Dimethoxy-2-[(4-methoxyphenyl)thio]benzoic acid

2-Bromo-4,5-dimethoxybenzoic acid (85 g, 0.326 mol) and 4-methoxybenzenethiol (50 g, 0.359 mol) were dissolved in amyl alcohol (1275 ml), under a nitrogen atmosphere. To this solution was added anhydrous potassium carbonate (146.3 g, 1.06 mol), and anhydrous copper (II) acetate (15 g). The mixture was then heated at reflux for 24 hours, by which time a TLC (toluene/ethyl acetate/formic acid 5:4:1) showed the reaction to be virtually complete. The solvent was removed under high vacuum, and the residue was dissolved in water (2 lt). This was then filtered to remove suspended solids, which were retained. The aqueous phase was extracted with t-butyl methyl ether (3×500 ml) and this was set aside. The aqueous phase was acidified to pH 1 with 32% hydrochloric acid, and the product was extracted out with ethyl acetate (3×1 lt), the combined organic extracts were dried over sodium sulphate, filtered and concentrated to brown oily solid. This was triturated with t-butyl methyl ether, and collected by filtration. This was dried to give a pale pink solid, 31 g @33.66% by HPLC.

The yellow solid from the initial filtration (72 g) was treated with hydrochloric acid and the product extracted into a mixture of tetrahydrofuran and ethyl acetate (1:1) (4 lt). This was dried over sodium sulphate, filtered and concentrated to a yellow solid which gradually turned grey/green. This was triturated with ethanol, collected by filtration and washed on the filter with ethanol and t-butyl methyl ether. This was dried to a grey solid 47 g @85.41%.

The filtrates were concentrated to get a small second crop, of white solid 4 g @98.17%. This was subjected to Proton NMR, which confirmed the product to be that which was desired.

Stage II: 2,3,7-Trimethoxy-9H-thioxanthene

Trial 1

To stirred 95% sulphuric acid (10 ml) was added 4,5-dimethoxy-2-[(4-methoxyphenyl)thio]benzoic acid, second crop (1 g, 0.0031 mol), and the mixture stirred overnight at room temperature. TLC showed the reaction to be complete, so the reaction mixture was poured onto ice (100 g). The product was extracted out with ethyl acetate (3×100 ml) and the combined organic extracts were washed with saturated sodium bicarbonate solution (100 ml), then dried over sodium sulphate, and filtered. The solvent was removed under reduced pressure to leave a yellow solid, 0.2 g @76.1% by HPLC.

Trial 2

To stirred 95% sulphuric acid (50 ml) was added 4,5-dimethoxy-2-[(4-methoxyphenyl)thio]benzoic acid, first crop (5 g, 0.0156 mol), and the mixture stirred overnight at room temperature. TLC showed the reaction to be complete, so the reaction mixture was poured onto ice (300 g). The product was extracted out with ethyl acetate (3×200 ml) and the combined organic extracts were washed with 10% potassium hydroxide solution (2×100 ml), then dried over sodium sulphate, and filtered. The solvent was removed under reduced pressure to leave a pale yellow solid, 0.5 g @85.1% by HPLC.

The two products were combined and dissolved in tetrahydrofuran (250 ml), and then stirred with 10% potassium hydroxide solution (150 ml). The two layers were separated and the aqueous was extracted with ethyl acetate (2×100 ml). The combined organics were dried over sodium sulphate, filtered and concentrated to a yellow solid. This was dissolved in refluxing toluene (70 ml) and filtered hot through a GF/F fibre pad. After cooling to room temperature overnight, no solid was present. The solution was concentrated to ⅓ volume and left to cool. The solid was collected by filtration, washed with t-butyl methyl ether, this was dried to give 690 mg @93.43%.

Figure 4:
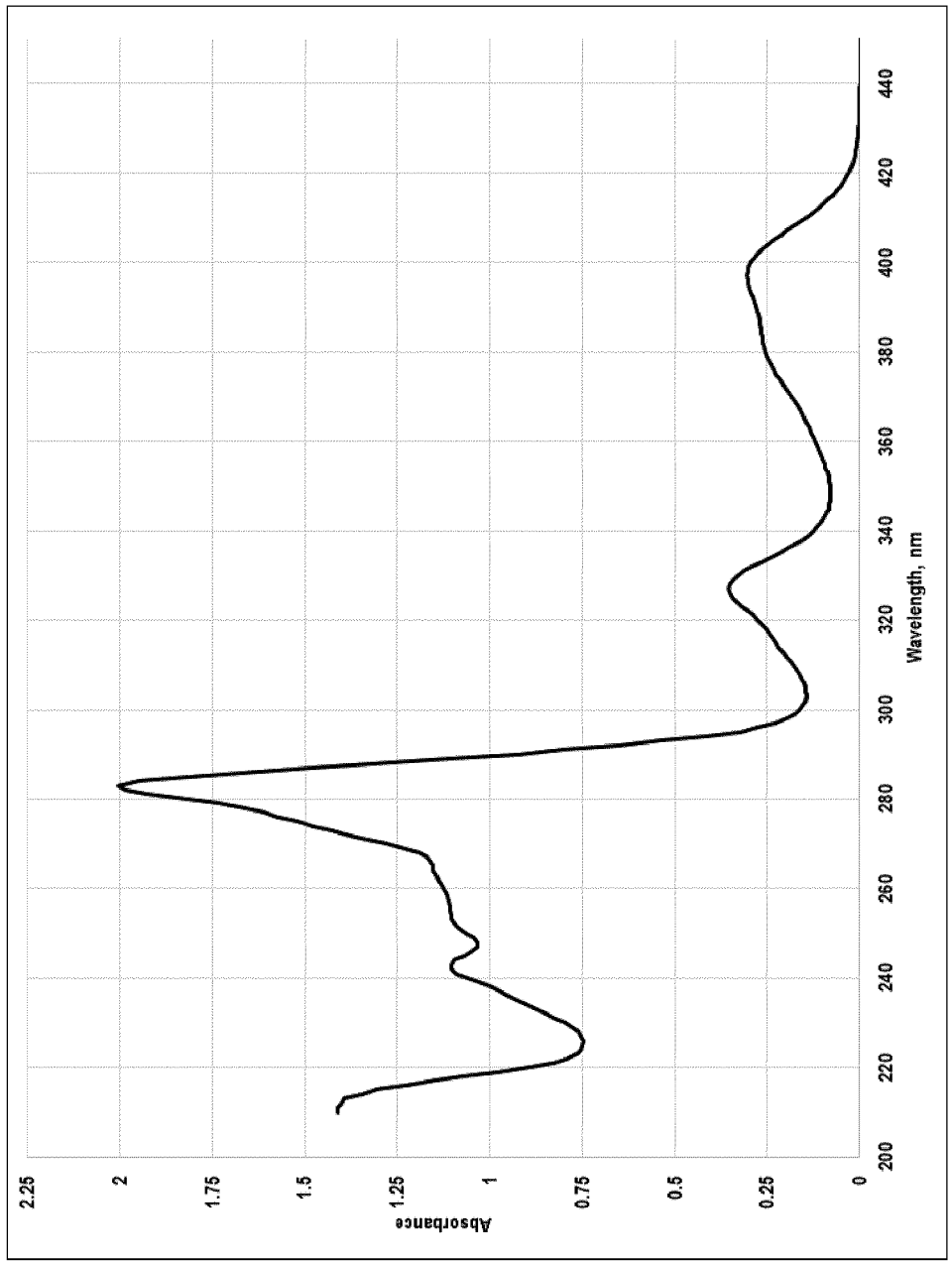
Figure 5:
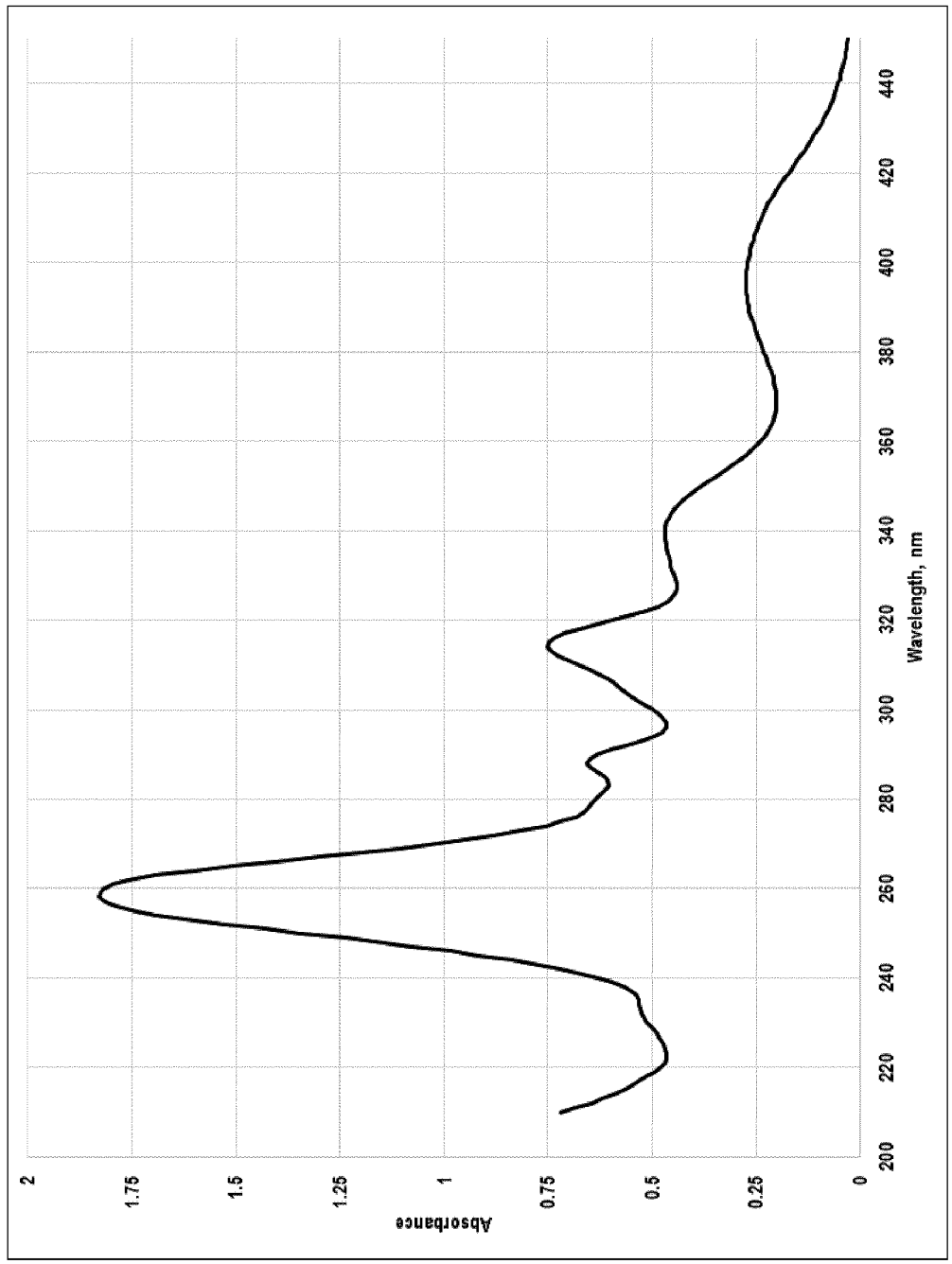

The UV absorbance spectrum for this compound is shown in FIG. 4.

Example 11

Synthesis of: 3,4-Bis(benzyloxy)-9H-thioxanthen-9-one

To a solution of 3,4-dihydroxy-9H-thioxanthen-9-one (34 g, 0.139 mol) in acetone (850 ml) was added anhydrous potassium carbonate (119 g, 0.861 mol, 6.2 eq.), under a nitrogen atmosphere.

The mixture was heated to reflux and benzyl chloride (60 g, 0.474 mol. 3.4 eq) was added dropwise over ~2 hours. The reaction was then refluxed overnight (~18 hours). The reaction was checked by TLC (hexane/ethyl acetate 1:1), and found to be almost complete. A further 5 g of benzyl chloride was added and the reaction refluxed for a further 2 hours, after which time the reaction was complete.

The reaction mixture was cooled to room temperature, then poured into demineralised water (5.1 lt), and stirred for 10 minutes. The resulting solid was collected by filtration, and washed on the filter with demineralised water (~1 lt), then barrier washed with hexane (~500 ml). The off white solid was stirred for 10 minutes with ethanol, (200 ml), and again collected by filtration, pulled dry then washed with t-butyl methyl ether. The solid was dried to constant weight.

Yield 54 g, 0.127 mol, 91.4%, purity by HPLC was 99.24%.

Example 13

Synthesis of: 3,4-Bis(1-ethoxyethyl)-9H-thioxanthen-9-one 3,4-Dihydroxy-9H-thioxanthen-9-one (5 g, 20.5 mmol), was suspended in diethyl ether (50 ml) under a nitrogen atmosphere. To this was added ethyl vinyl ether (7.4 g, 102.5 mmol, 5 eq.) and trifluoroacetic acid (0.24 g, 2.05 mmol).

The mixture was stirred at ambient temperature for 4 days. The mixture was still a suspension and TLC indicated that starting material was still left, so tetrahydrofuran (25 ml) was added (did not dissolve). Also added was ethyl vinyl ether (10 g, 139 mmol) and 10 drops of trifluoroacetic acid.

The reaction was further stirred for 24 hours, and was then found to be in solution, and all the starting material had been consumed. Two upper spots were present, a further charge of ethyl vinyl ether (7.4 g, 102.5 mmol) was added and the reaction stirred for a further 24 hours, with no change.

The reaction mixture was neutralised by addition of triethylamine (~0.5 ml) and stirred for a further 1 hour. The reaction mixture was filtered through a GF/F fibre pad to remove some trace insoluble. The reaction mixture was concentrated to a thick brown syrup, trace solvent blown away with nitrogen.

Yield 7 g. A sample was submitted for $^1$H NMR, which indicated that the correct product was present (along with some minor impurities and solvent residue).

Example 14

Synthesis of: 3',4'-Dimethoxyspiro[(1,3)-dioxane-2, 9'-thioxanthene]

Stage I: 3,4-Dimethoxy-9H-thioxanthen-9-thione 3,4-dimethoxy-9H-thioxanthen-9-one (10 g, 36.7 mmol) was suspended in toluene (300 ml), to this was added Lawessons reagent (11 g, 27.2 mmol). The mixture was heated at 80° C. under a nitrogen atmosphere, and followed by TLC. The reaction was complete in less than 1 hour.

The reaction was cooled to room temperature and poured into water (1000 ml), the toluene layer was separated off and the aqueous layer was extracted with ethyl acetate (3×300 ml). The combined organic extracts were washed with brine (500 ml), and dried over sodium sulphate. The drying agent was removed by filtration and the solvent was removed in vacuo to leave a dark green solid. This was triturated with t-butyl methyl ether and collected by filtration and washed with a few ml of t-butyl methyl ether.

The green solid was dried in air to leave 9 g, 85%, with a purity by HPLC of 94.71%.

Stage II: 3',4'-Dimethoxyspiro[(1,3)-dioxane-2,9'-thioxanthene]

3,4-Dimethoxy-9H-thioxanthen-9-thione (9 g, 31.2 mmol) was suspended in acetonitrile (200 ml).

Under a nitrogen atmosphere was added 1,3-propanediol (3.3 g, 43.4 mmol), and triethylamine (17 ml). The mixture was stirred and silver trifluoroacetate (26.1 g) was added. A colour change from green to red occurred and a rise in temperature (13.8-25.6° C.) was observed. After one hour a TLC (2:1 hexane/ethyl acetate) showed no starting material left, with two product spots (GC, 68.86%, and 26.78% corresponding to the original ketone).

The acetonitrile was evaporated off and the residue was partitioned between brine (200 ml) and ethyl acetate (200 ml), and then filtered through a GF/F to remove inorganics. The filter cake was washed with ethyl acetate (2×100 ml). The two layers were separated and the aqueous layer was extracted with ethyl acetate (2×100 ml). The combined organic extracts were dried over sodium sulphate and then filtered to remove the drying agent.

The clear solution was concentrated to leave an orange/brown solid, 9 g.

This was dissolved in isopropyl alcohol (260 ml) and sodium borohydride (8 g, 211 mmol) was added, under nitrogen the reaction was stirred overnight at 50° C. A GC showed there to be 6.15% ketone and 19.65% alcohol so the reaction was cooled to room temperature and poured into saturated brine (400 ml). The product was extracted out with ethyl acetate (3×300 ml) and the combined organic extracts were dried over sodium sulphate, filtered and concentrated to a white solid 5 g. This was recrystallized from ethanol (80 ml) and allowed to cool in the fridge for several hours. The solid was collected by filtration and washed on the filter with small volumes of ethanol and t-butyl methyl ether. The solid was dried at 50° C. in the vacuum oven.

Yield was 4.4 g, 42.7%. Purity by GC was 97.8% and by HPLC 98.94%. The product conformed to structure by $^1$H NMR.

Example 15

Synthesis of: Di-t-butyl (9-thioxo-9H-thioxanthene-3,4-diyl)dicarbonate

Stage I: Di-t-butyl (9-oxo-9H-thioxanthene-3,4-diyl) dicarbonate 3,4-Dihydroxy-9H-thioxanthen-9-one (5 g, 20.5 mmol) was suspended in acetonitrile (50 ml), and stirred under nitrogen. To this was added di-t-butyldicarbonate (11.2 g, 51.3 mmol), and 4-dimethylaminopyridine (1.25 g, 10.25 mmol). The mixture was stirred at room temperature and followed by TLC. Initially vigorous effervescence occurred and the solids dissolved to give a dark brown solution. A TLC after (1:1, hexane/ethyl acetate) showed the reaction to be complete after 30 minutes. The reaction mixture was filtered through GF/F and the solvents stripped off to leave a thick syrup which was and triturated/crystallised from ethanol. Solid was collected by filtration, washed on the filter with ethanol and t-butyl methyl ether, and dried, to give 4 g, which was used in the next step immediately.

Stage II: Di-t-butyl (9-thioxo-9H-thioxanthene-3,4-diyl)dicarbonate

The crude material from above (4 g, 9 mmol) was dissolved in toluene (80 ml) and to this was added Lawessons reagent (2.6 g). The mixture was heated at 80° C. under a nitrogen atmosphere for 30 minutes. A TLC (2:1 hexane/ethyl acetate) showed the reaction to be complete.

The reaction mixture was cooled to room temperature, and poured into saturated sodium bicarbonate solution (200 ml). The organic layer was separated off and the aqueous layer was extracted with ethyl acetate (2×100 ml), and the combined organic extracts were washed with brine (200 ml). The extracts were dried over sodium sulphate and filtered through a GF/F fibre pad, the solvent was removed in vacuo to leave a green oil (assume 9 mmol) which was directly in the next step below.

Stage: III: Di-t-butylspiro[(1,3)-dioxolane-2,9'-thioxanthene]-3',4'-diyl dicarbonate Di-t-butyl (9-thioxo-9H-thioxanthene-3,4-diyl)dicarbonate (assume 9 mmol) from above was dissolved in acetonitrile (80 ml) under a nitrogen atmosphere. To this was added ethylene glycol (1 g, 16 mmol) and triethylamine (6 ml), followed by silver trifluoroacetate (7.6 g). The mixture was stirred at ambient temperature for 1 hour, and then checked by TLC (2:1, hexane/ethyl acetate) and shown to be complete.

The acetonitrile was evaporated off and the residue was partitioned between brine (200 ml) and ethyl acetate (200 ml). The mixture was filtered through a GF/F and separated. The aqueous layer was extracted with ethyl acetate (2×50 ml), and the organic layer dried over sodium sulphate.

The solvent was removed and the resulting brown residue was purified on the "Jones" column.

This gave 1.8 g of material, which was sent for $^1$H NMR this agreed with the expected structure but contained residual solvent, which was removed under high vacuum.

The invention claimed is:

1. A compound of the formula I:

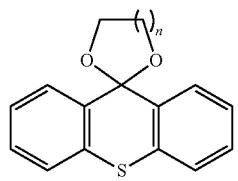

(I)

wherein n=1, 2, 3, 4 or 5; or
a compound of the formula (Ia):

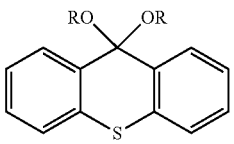

(Ia)

wherein R=methyl, ethyl or propyl, and
wherein one of the aromatic rings in the compound of formula I or the compound of formula Ia is substituted with at least two substituents independently selected from hydroxy, alkoxy, benzyloxy, alkylcarbonate, hydroxyalkyl, acetal, ester, oxyacetic acid and esters thereof, aryloxy or arylthio, and the other aromatic ring is unsubstituted or is substituted with at least one substituent independently selected from hydroxy, alkoxy, benzyloxy, alkylcarbonate, hydroxyalkyl, acetal, ester, oxyacetic acid and esters thereof, aryloxy and arylthio.

2. The compound according to claim 1, wherein one aromatic ring is substituted with a single substituent selected from hydroxy, alkoxy, benzyloxy, alkylcarbonate, hydroxyalkyl, acetal, ester, oxyacetic acid and esters thereof, aryloxy or arylthio.

3. The compound according to claim 1, wherein one aromatic ring is substituted with three substituents independently selected from hydroxy, alkoxy, benzyloxy, alkylcarbonate, hydroxyalkyl, acetal, ester, oxyacetic acid and esters thereof, aryloxy or arylthio.

4. The compound according to claim 1, wherein one aromatic ring is substituted with four substituents independently selected from hydroxy, alkoxy, benzyloxy, alkylcarbonate, hydroxyalkyl, acetal, ester, oxyacetic acid and esters thereof, aryloxy or arylthio.

5. The compound according to claim 1, wherein each of the aromatic rings is substituted with at least one substituent independently selected from hydroxy, alkoxy, benzyloxy, alkylcarbonate, hydroxyalkyl, acetal, ester, oxyacetic acid and esters thereof, aryloxy or arylthio.

6. The compound according to claim 1, wherein one of the aromatic rings is substituted with two substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with one, two, three or four substituents selected from hydroxy, alkoxy, benzyloxy, alkylcarbonate, hydroxyalkyl, acetal, ester, oxyacetic acid and esters thereof, aryloxy or arylthio.

7. The compound according to claim 1, wherein one of the aromatic rings is substituted with three substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with one, two, three or four substituents selected from hydroxy, alkoxy, benzyloxy, alkylcarbonate, hydroxyalkyl, acetal, ester, oxyacetic acid and esters thereof, aryloxy or arylthio.

8. The compound according to claim 1, wherein one of the aromatic rings is substituted with four substituents independently selected from hydroxy, alkoxy, benzyloxy, alkylcarbonate, hydroxyalkyl, acetal, ester, oxyacetic acid and esters thereof, aryloxy and arylthio, and the other one of the rings is substituted with one, two, three or four substituents independently selected from hydroxy, alkoxy, benzyloxy, alkylcarbonate, hydroxyalkyl, acetal, ester, oxyacetic acid and esters thereof, aryloxy or arylthio.

9. The compound according claim 1, wherein the alkoxy is a C1-4 alkoxy.

10. The compound according to claim 1, wherein the hydroxyalkyl is a hydroxy (C1-4) alkyl group.

11. The compound according to claim 1, wherein the alkyl carbonate is a C1-4 alkylcarbonate.

12. The compound according claim 1, wherein the ester is a C1-4 alkyl ester.

13. The compound according to claim 1, wherein the acetal is a $C_{1-4}$alkyl(alkoxy)$_2$ group.

14. The compound according to claim 1, wherein the substituents on the aromatic ring or rings must only be selected from the group consisting of hydroxy and alkoxy groups.

15. The compound according to claim 1, wherein all of the substituents are the same.

16. The compound according to claim 1, which is selected from: 3',4'-dimethoxyspiro[1,3-dioxane-2,9'-thioxanthene], 3',4'-dimethoxyspiro[1,3-dioxolane-2,9'-thioxanthene], 2',3'-dimethoxyspiro[(1.3)-dioxolane-2,9'-thioxanthene], methane; 2'-methoxy-5,6-dimethyl-spiro[1,3-dioxepane-2,6'-thiochromeno[3,2-g][1,3]benzodioxole], 2'-methoxyspiro[1,3-dioxane-2,6'-thiochromeno[3,2-g][1,3]benzodioxole], 2'-methoxyspiro[1,3-dioxepane-2,6'-thiochromeno[2,3-g][1,3]benzodioxole], 2'-methoxy-5,5-dimethyl-spiro[1,3-dioxane-2,6'-thiochromeno[2,3-e][1,3]benzodioxole], 2'-methoxy-4,6-dimethyl-spiro[1,3-dioxane-2,6'-thiochromeno[3,2-g][1,3]benzodioxole], 2'-methoxy-4,7-dimethyl-spiro[1,3-dioxepane-2,6'-thiochromeno[2,3-e][1,3]benzodioxole], 2'-methoxy-5,5-dimethyl-spiro[1,3-dioxepane-2,6'-thiochromeno[2,3-e][1,3]benzodioxole], 2'-methoxy-5-methyl-spiro[1,3-dioxepane-2,6'-thiochromeno[2,3-e][1,3]benzodioxole], 2'-ethoxyspiro[1,3-dioxepane-2,6'-thiochromeno[2,3-e][1,3]benzodioxole], 2'-propoxyspiro[1,3-dioxepane-2,6'-thiochromeno[3,2-g][1,3]benzodioxole], 2'-phenoxyspiro[1,3-dioxepane-2,6'-thiochromeno[2,3-e][1,3]benzodioxole], 2'-isopropoxyspiro[1,3-dioxepane-2,6'- thiochromeno[2,3-e][1,3]benzodioxole], 2'-ethoxyspiro[1,3-dioxane-2,6'-thiochromeno[3,2-g][1,3]benzodioxole], 2'-ethoxyspiro[1,3-dioxolane-2,6'-thiochromeno[2,3-e][1,3]benzodioxole], 2'-propoxyspiro[1,3-dioxane-2,6'-thiochromeno[3,2-g][1,3]benzodioxole], 2'-propoxyspiro[1,3-dioxolane-2,6'-thiochromeno[2,3-e][1,3]benzodioxole], 2'-isopropoxyspiro[1,3-dioxane-2,6'-thiochromeno[2,3-e][1,3]benzodioxole], 2'-isopropoxyspiro[1,3-dioxolane-2,6'-thiochromeno[3,2-g][1,3]benzodioxole], 2'-methoxyspiro[1,3-dioxane-2,6'-thiochromeno[2,3-e][1,3]benzodioxole], 2'-methoxyspiro[1,3-dioxolane-2,6'-thiochromeno[2,3-e][1,3]benzodioxole], spiro[1,3-dioxolane-2,9'-thioxanthene]-3',4'-diol, spiro[1,3-dioxane-2,9'-thioxanthene]-3',4'-diol, spiro[1,3-dioxepane-2,9'-thioxanthene]-3',4'-diol, 5-methylspiro[1,3-dioxepane-2,9'-thioxanthene]-3',4'-diol, 5,5-dimethylspiro[1,3-dioxepane-2,9'-thioxanthene]-3',4'-diol, 3',4'-dimethoxy-4,6-dimethyl-spiro[1,3-dioxane-2,9'-thioxanthene], 3',4'-dimethoxy-4,5-dimethyl-spiro[1,3-dioxolane-2,9'-thioxanthene], 9,9-diethoxy-3,4-dimethoxy-thioxanthene, 2-methoxy-6,6-dipropoxy-thiochromeno[3,2-g][1,3]benzodioxole and 6,6-diethoxy-2-methoxy-thiochromeno[2,3-e][1,3]benzodioxole.

\* \* \* \* \*